(12) United States Patent
Kitagawa et al.

(10) Patent No.: US 9,452,417 B2
(45) Date of Patent: Sep. 27, 2016

(54) CATALYST USING PD-RU SOLID SOLUTION ALLOY FINE PARTICLES

(71) Applicant: Japan Science and Technology Agency, Saitama (JP)

(72) Inventors: Hiroshi Kitagawa, Nara (JP); Kohei Kusada, Kyoto (JP); Katsutoshi Nagaoka, Oita (JP); Katsutoshi Sato, Oita (JP); Md. Shahajahan Kutubi, Oita (JP)

(73) Assignee: Japan Science and Technology Agency, Saitama (JP)

( * ) Notice: Subject to any disclaimer, the term of this patent is extended or adjusted under 35 U.S.C. 154(b) by 0 days.

(21) Appl. No.: 14/429,255

(22) PCT Filed: Sep. 18, 2013

(86) PCT No.: PCT/JP2013/005512
§ 371 (c)(1),
(2) Date: Mar. 18, 2015

(87) PCT Pub. No.: WO2014/045570
PCT Pub. Date: Mar. 27, 2014

(65) Prior Publication Data
US 2015/0231605 A1    Aug. 20, 2015

(30) Foreign Application Priority Data
Sep. 18, 2012   (JP) ................................. 2012-204292
Mar. 8, 2013    (JP) ................................. 2013-046885

(51) Int. Cl.
*B01J 23/46*   (2006.01)
*B01J 37/08*   (2006.01)
*C07C 1/32*    (2006.01)
*C07C 37/16*   (2006.01)
*C07C 45/61*   (2006.01)
*C07C 45/64*   (2006.01)

(52) U.S. Cl.
CPC .............. *B01J 23/462* (2013.01); *B01J 37/08* (2013.01); *C07C 1/321* (2013.01); *C07C 37/16* (2013.01); *C07C 45/61* (2013.01); *C07C 45/64* (2013.01); *C07C 2523/46* (2013.01)

(58) Field of Classification Search
CPC ........ B01J 23/462; B01J 23/46; B01J 23/44; B01J 37/08
See application file for complete search history.

(56) References Cited

U.S. PATENT DOCUMENTS

2001/0026782 A1*  10/2001  Wang .................... B01J 12/007
                                                                422/211
2008/0318765 A1   12/2008  Aradi et al.

FOREIGN PATENT DOCUMENTS

| JP | H11-207180 A | 8/1999 |
| JP | 2001-224965 A | 8/2001 |
| JP | 2001224965 A * | 8/2001 |
| JP | 2003-080070 A | 3/2003 |
| JP | 2005-161186 A | 6/2005 |
| JP | 2009-001901 A | 1/2009 |
| JP | 2009-545114 A | 12/2009 |
| WO | WO-2008/012572 A2 | 1/2008 |

OTHER PUBLICATIONS

English translation of JP2001-224965A, Specification (2001).*
Kusada, Kobayashi and Kitagawa, "The Synthesis and Properties of Noble PdRu Solis-solution Alloy Nanoperticles", Proceedings of the 92th Annual Spring Meeting of The Chemical Society of Japan, 2012.
Kusada, Kobayashi and Kitagawa, "Synthesis and Structure of Pd-Ru Alloy Nanoparticles", Abstract of the Presentation No. 1P064, the 4th Annual Meeting of Japan Society for Molecular Science, 2010.
International Search Report issued in Application No. PCT/JP2013/005512, mailed Jan. 7, 2014.
Office Action issued in Chinese Application No. 201380048273.7, dated Jan. 25, 2016.
P. Kedzierzawski et al., "Novel Metastable Pd-Ru Catalysts for electrooxidation of formic acid," Institute of Physical Chemestry, ECS Transactions, vol. 28, No. 8, 2010, p. 23-31.
"Alloy Noble Metal Nanoparticles and Their Structures," a copy of the web page of Laboratory of Novel Materials Hybrid Engineering, Research Group of Materials Design, Division of Materials Science and Engineering, Graduate School/Faculty of Engineering, Hokkaido University (available at http://labs.eng.hokudai.ac.jp/labo/limsa/?page_id=1753).

* cited by examiner

*Primary Examiner* — Yong Chu
(74) *Attorney, Agent, or Firm* — Michael Best & Friedrich LLP

(57) ABSTRACT

The catalyst disclosed is a catalyst including palladium-ruthenium alloy fine particles in which palladium and ruthenium form a solid solution. The palladium-ruthenium alloy fine particles used in this catalyst can be produced by a production method including the step of maintaining a solution containing a protective agent, a reducing agent, a palladium compound or palladium ions, and a ruthenium compound or ruthenium ions at a temperature equal to or higher than a predetermined temperature.

14 Claims, 27 Drawing Sheets

Pd$_{0.5}$-Ru$_{0.5}$ alloy fine particles
HAADF-STEM image

Pd$_{0.5}$-Ru$_{0.5}$ alloy fine particles
Ru-L EDX map

Pd$_{0.5}$-Ru$_{0.5}$ alloy fine particles
Pd-L EDX map

Pd$_{0.5}$-Ru$_{0.5}$ alloy fine particles
Ru-L + Pd-L EDX map $Pd_{0.1}$-$Ru_{0.9}$ alloy fine particles
Pd-L EDX map $Pd_{0.1}$-$Ru_{0.9}$ alloy fine particles
Ru-L + Pd-L EDX map Pd$_{0.3}$-Ru$_{0.7}$ alloy fine particles
HAADF-STEM image Pd$_{0.3}$-Ru$_{0.7}$ alloy fine particles
Ru-L EDX map Pd$_{0.3}$-Ru$_{0.7}$ alloy fine particles
Pd-L EDX map Pd$_{0.3}$-Ru$_{0.7}$ alloy fine particles
Ru-L + Pd-L EDX map Pd$_{0.7}$-Ru$_{0.3}$ alloy fine particles
HAADF-STEM image Pd$_{0.7}$-Ru$_{0.3}$ alloy fine particles
Ru-L EDX map Pd$_{0.7}$-Ru$_{0.3}$ alloy fine particles
Pd-L EDX map Pd$_{0.7}$-Ru$_{0.3}$ alloy fine particles
Ru-L + Pd-L EDX map

CATALYST USING PD-RU SOLID SOLUTION ALLOY FINE PARTICLES

TECHNICAL FIELD

The present invention relates to a catalyst using Pd—Ru solid solution alloy fine particles, a method for producing the Pd—Ru solid solution alloy fine particles, and a method for producing an organic compound by using the catalyst.

BACKGROUND ART

Palladium fine particles are used as a catalyst (three-way catalyst) for purification of exhaust gas of automobiles (e.g., Patent Literature 1). However, when palladium fine particles are used as a catalyst, a problem arises in that their performance is significantly deteriorated due to poisoning by carbon monoxide etc. Rhodium fine particles are also used as a catalyst; however, they have the disadvantage of being expensive.

Catalysts using alloy fine particles have conventionally been proposed (Patent Literature 2 and 3). In addition, methods for producing Pd—Ru alloy fine particles have been proposed (Non Patent Literature 1 and 2).

Furthermore, Suzuki-Miyaura cross-coupling using Pd or the like as a catalyst has conventionally been practiced widely. In Suzuki-Miyaura cross-coupling reactions, it is important to inhibit a homocoupling reaction.

CITATION LIST

Patent Literature

Patent Literature 1: JP 11(1999)-207180 A
Patent Literature 2: JP 2005-161186 A
Patent Literature 3: JP 2009-545114 A

Non Patent Literature

Non Patent Literature 1: "Synthesis and Properties of Novel Pd—Ru Solid Solution Alloy Nanoparticles", Proceedings of the 92th Annual Spring Meeting of The Chemical Society of Japan (2012)
Non Patent Literature 2: Abstract of the Presentation No. 1P064 (Synthesis and Structure of Pd—Ru Alloy Nanoparticles), the 4th Annual Meeting of Japan Society for Molecular Science (2010)

SUMMARY OF INVENTION

Technical Problem

Under such circumstances, an object of the present invention is to provide a novel catalyst and a method for producing the catalyst. Another object of the present invention is to provide a method for producing an organic compound by using the catalyst of the present invention.

Solution to Problem

The present inventors have found that it is possible to produce alloy fine particles in which a solid solution is formed by palladium and rhodium which usually do not form a solid solution, and that it is possible to use the alloy fine particles as a novel catalyst. The present invention is based on these new findings.

The present invention provides a catalyst, and the catalyst includes palladium-ruthenium alloy fine particles in which palladium and ruthenium form a solid solution.

In addition, the present invention provides a method for producing palladium-ruthenium alloy fine particles in which palladium and ruthenium form a solid station. This production method includes the step of maintaining a solution containing a protective agent, a reducing agent, a palladium compound or palladium ions, and a ruthenium compound or ruthenium ions at a temperature equal to or higher than a predetermined temperature.

Advantageous Effects of Invention

According to the present invention, it is possible to obtain a catalyst that has a high catalytic activity for oxidation reaction of carbon monoxide, reduction reaction of nitrogen oxide, oxidation reaction of hydrogen gas, oxidation reaction of hydrocarbon, and the like. As described later, the Pd—Ru alloy fine particles exhibit, for oxidation reaction of carbon monoxide, a marked catalytic activity that is higher than the catalytic activity of any of Pd fine particles, Ru fine particles, and a mixture of Pd fine particles and Ru fine particles.

DESCRIPTION OF EMBODIMENTS

Figure 1:
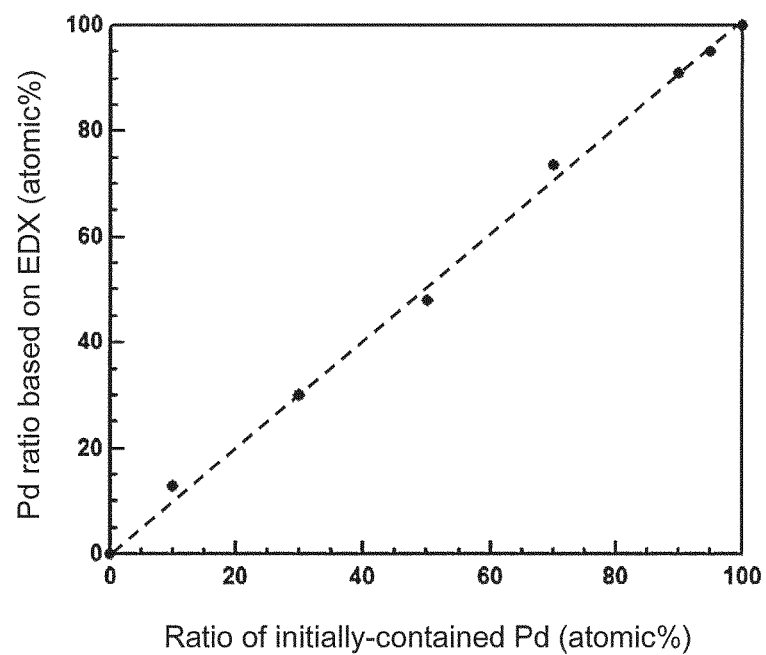
FIG. 1 is a graph showing the relationship in an example between the ratio of initially-contained Pd and the measured value of the ratio of Pd in the produced Pd—Ru alloy fine particles.

Hereinafter, embodiments of the present invention will be described with reference to examples. The present invention is not limited to the embodiments and examples presented below. In the following description, specific numerical values or specific materials are mentioned as examples in some cases; however, other numerical values or other materials may be employed as long as the effects of the present invention can be obtained.

(Catalyst)

The catalyst of the present invention includes alloy fine particles in which palladium (Pd) and ruthenium (Ru) form a solid solution. That is, the catalyst of the present invention includes palladium-ruthenium solid solution alloy fine particles. The solid solution alloy fine particles may be hereinafter referred to as "Pd—Ru alloy fine particles".

In the Pd—Ru alloy fine particles, Pd and Ru are not phase-separated but form a solid solution. As a result of the formation of a solid solution of Pd and Ru, properties different from those of Pd or Ru bulks are exhibited. Therefore, the use of the Pd—Ru alloy fine particles makes it possible to obtain a catalytic activity different from that of mixed particles of Pd fine particles and Ru fine particles.

The average particle diameter of the Pd—Ru alloy fine particles may be in the range of 1 nm to 50 nm or in the range of 1 nm to 10 nm. When the composition of the Pd—Ru alloy fine particles is represented by the formula $Pd_xRu_{1-x}$, x may satisfy $0.01 \leq x \leq 0.99$, $0.1 \leq x\ 0.9$, or $0.3 \leq x \leq 0.7$. The particle diameter and the composition ratio can easily be adjusted by changing the production conditions.

The Pd—Ru alloy fine particles can be used as an oxidation catalyst for carbon monoxide. Pd can be used as a catalyst for purification of exhaust gas of automobiles, but suffers from the problem of poisoning by carbon monoxide. The Pd—Ru alloy fine particles have a function as an oxidation catalyst for carbon monoxide; therefore, the use of the Pd—Ru alloy fine particles as a catalyst for purification of exhaust gas can be expected to reduce the influence of poisoning by carbon monoxide.

The Pd—Ru alloy fine particles are expected to exert a variety of catalytic actions; for example, the Pd—Ru alloy fine particles are expected to be used as an oxidation catalyst or a reduction catalyst. For example, the Pd—Ru alloy fine particles can be used as a reduction catalyst for nitrogen oxide ($NO_x$), an oxidation catalyst for hydrocarbon (HC), and an oxidation catalyst for hydrogen gas. Therefore, the Pd—Ru alloy fine particles are expected to be used as a purification catalyst for exhaust gas of automobiles etc. or as an electrode catalyst of a fuel cell. As thus far described, the Pd—Ru alloy fine particles can be used as at least one catalyst selected from the group consisting of an oxidation catalyst for carbon monoxide, a reduction catalyst for nitrogen oxide, an oxidation catalyst for hydrocarbon, and an oxidation catalyst for hydrogen gas.

The Pd—Ru alloy fine particles may be used as a catalyst for Suzuki-Miyaura cross-coupling. In another aspect, the present invention relates to a method for producing an organic compound, the method including performing Suzuki-Miyaura cross-coupling by using the Pd—Ru alloy fine particles as a catalyst.

There is no particular limitation on the compounds to be coupled by the Suzuki-Miyaura cross-coupling and on the coupling conditions. Commonly-known compounds and conditions may be employed. The following gives examples of the compounds to be coupled and the coupling conditions; however, the present invention is not limited by the compounds and conditions described below.

Example of Suzuki-Miyaura Cross-Coupling

In the Suzuki-Miyaura cross-coupling, an organic compound such as an organic halide and an organic boron compound are coupled. Hereinafter, the organic boron compound may be referred to as a "compound (B)", and the compound to be coupled with the organic boron compound may be referred to as a "compound (A)".

A typical compound (A) is represented by the formula $R^1$—X. Examples of $R^1$ include aryl groups, and specifically include a phenyl group, a phenyl group to which a substituent is bonded, a trimethylsilyl group, a triflate group, and a tosyl group. Examples of X include halogen groups. Typical examples of the compound (A) include aryl halides. An example of the compound (A) is represented by the formula (I) below.

[Chemical formula 1]

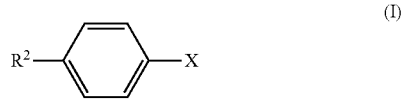

(I)

For the above formula (I), examples of $R^2$ include a hydrogen atom, a methyl group, a methoxy group, an acetyl group, a cyano group, a fluoro group, and a nitro group. Examples of X include I, Br, and Cl, and I and Br are preferably used.

The compound (B) is an organic boron compound such as boronic acid, a boronic acid ester, and an alkylborane. A typical compound (B) is represented by the formula $R^3$-G. Examples of $R^3$ include aryl groups, and specifically include a phenyl group and a phenyl group to which a substituent is bonded. Examples of G include —B(OH)$_2$ (boronic acid), esters thereof, and —BR$^a$R$^b$ (R$^a$ and R$^b$ are each an alkyl group, and may be the same or different). An example of the compound (B) is represented by the formula (II) below.

[Chemical formula 2]

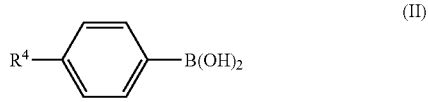

(II)

For the above formula (II), examples of $R^4$ include a hydrogen atom, a methyl group, a methoxy group, a cyano group, a fluoro group, and a nitro group.

By the above formulae (I) and (II), examples in which substituents are introduced at the para positions are represented; however, they may be introduced at other substituent positions.

By the cross-coupling of the compound (A) and the compound (B), the different compounds can be bonded together. When $R^1$ and $R^3$ are different (for example, when $R^2$ and $R^4$ are different), different atom groups can be bonded together by the cross-coupling of the compound (A) and the compound (B). In the Suzuki-Miyaura cross-coupling, it is important to inhibit a reaction between the molecules of the compound (A) and a reaction between the molecules of the compound (B) so as to increase the yield of the cross-coupling reaction. The compound (A) and the compound (B) contained in a starting material may be in equimolar amounts, or either of them may be contained in a larger amount. For example, the number of moles of the compound (B) contained in the starting material may be set greater than the number of moles of the compound (A).

In a preferred example of the present invention, the compound (A) and the compound (B) are cross-coupled in a solvent in the presence of the Pd—Ru alloy fine particles (catalyst) and a base. At this time, the solvent may be heated to promote the reaction.

There is no particular limitation on the base and the solvent. Any of commonly-known bases and solvents used for Suzuki-Miyaura cross-coupling may be used. Examples of the base include bases mentioned in EXAMPLES. Examples of the solvent include solvents mentioned in EXAMPLES. The solvent may contain a protective agent (PVP mentioned later, for example).

When the Pd—Ru alloy fine particles are used as a catalyst, the Pd—Ru alloy fine particles may be supported on a support. If the Pd—Ru alloy fine particles are supported on a support, aggregation of the nanoparticles during the reaction can be inhibited. There is no particular limitation on the support, and a commonly-known support may be used. For example, particles of alumina (Al$_2$O$_3$), titanium dioxide (TiO$_2$), magnesium oxide (MgO), cerium dioxide (CeO$_2$), praseodymium oxide (Pr$_6$O$_{11}$), or the like, may be used as the support.

The Pd—Ru alloy fine particles may be used as a catalyst without being supported on a support. When the Pd—Ru alloy fine particles are used as a catalyst in a solution, the Pd—Ru alloy fine particles may be protected by a protective agent (PVP mentioned later, for example).

(Method for Producing Catalyst)

An example of the method for producing the Pd—Ru alloy fine particles will be described hereinafter. The production method includes the step of maintaining a solution containing a protective agent, a reducing agent, a palladium compound or palladium ions, and a ruthenium compound or ruthenium ions at a temperature equal to or higher than a predetermined temperature. The predetermined temperature may be hereinafter referred to as "temperature (T)".

Examples of the protective agent include poly(N-vinyl-2-pyrrolidone) (which may be hereinafter referred to as "PVP"). Examples of the reducing agent include polyhydric alcohols such as triethylene glycol. Examples of the palladium compound include K$_2$[PdCl$_4$], Na$_2$[PdCl$_4$], and H$_2$[PdCl$_4$]. Examples of the ruthenium compound include RuCl$_3$.nH$_2$O, Na$_2$[RuCl$_6$], K$_2$[RuCl$_6$], (NH$_4$)$_3$[RuCl$_6$], and Ru(NO)(NO)$_3$.

When the protective agent is PVP, the number of moles of the monomer units of the PVP contained in the solution may be in the range of 1 to 10 times the total number of moles of Pd atoms and Ru atoms contained in the solution.

The temperature (T) may be, for example, 180° C., 190° C., or 200° C. The temperature at which the solution is maintained may be in the range of 180° C. to 230° C. or in the range of 180° C. to 220° C. The period of time during which the solution is maintained at a temperature equal to or higher than the temperature (T) may only be long enough for the Pd—Ru alloy fine particles to be formed. The period of time is, for example, 1 second or longer, and may be in the range of 5 seconds to 1 hour.

By the above step, the Pd—Ru alloy fine particles are formed. The alloy fine particles formed are washed, or supported onto a support, as necessary. There is no particular limitation on these steps, and commonly-known techniques may be employed. In the manner described above, the catalyst of the present invention is obtained.

An example of the production method of the present invention will be described hereinafter. In this example, a triethylene glycol solution (1) of PVP, and a solution (2) of a palladium compound and a ruthenium compound are prepared first. The solution (2) may be an aqueous solution. The palladium compound and the ruthenium compound may be compounds used in the examples described later.

Next, the solution (1) and the solution (2) are mixed, and the resulting mixed solution is maintained at a temperature equal to or higher than the temperature (T). In a preferred example, the solution (1) and the solution (2) are mixed by spraying the solution (2) into the solution (1) heated to a temperature equal to or higher than the temperature (T). As a result of the mixed solution being maintained at a temperature equal to or higher than the temperature (T) for a predetermined period of time, the Pd—Ru alloy fine particles are obtained.

EXAMPLES

Hereinafter, the present invention will be described in more detail by examples.

(Fabrication of Pd—Ru Alloy Fine Particles)

Several types of Pd—Ru alloy fine particles differing in composition ratio were fabricated and evaluated by the procedures described below.

First, 1.0 mmol of PVP functioning as a protective agent was dissolved in 100 ml of triethylene glycol functioning as a reducing agent and as a solvent; thus, a solution (1) was prepared. In addition, $K_2[PdCl_4]$ and $RuCl_3 \cdot nH_2O$ were dissolved in 40 mml of water to prepare an aqueous solution (2). At this time, $K_2[PdCl_4]$ and $RuCl_3 \cdot nH_2O$ were dissolved in 40 ml of water in a total amount of 1.0 mmol. The molar ratio between $K_2[PdCl_4]$ and $RuCl_3 \cdot nH_2O$ dissolved in the aqueous solution (2) was varied to change the composition ratio. Specifically, assuming that the molar ratio between $K_2[PdCl_4]$ and $RuCl_3 \cdot nH_2O$ dissolved was represented by y: 1−y, y was varied to 0.1, 0.3, 0.5, 0.7, 0.9, and 0.95.

Next, the solution (1) was heated to 200° C. Then, the aqueous solution (2) was sprayed by a spraying device into the solution (1) having a temperature of 200° C., and thus a mixed solution was obtained. After completion of the spraying, the temperature of the mixed solution was maintained at 200° C. for 5 to 15 minutes. For example, in the case of fabricating $Pd_{0.5}$—$Ru_{0.5}$ alloy fine particles, the maintenance of the temperature was done for 5 minutes. Thereafter, the mixed solution was left to cool to room temperature, and then the alloy fine particles in the mixed solution were separated from the solution by centrifugation. In this manner, several types of alloy fine particles differing in composition were fabricated. For comparison, fine particles consisting only of Pd and fine particles consisting only of Ru were also fabricated in the same manner as above.

Element analysis was performed on the obtained alloy fine particles. The results of the element analysis are shown in FIG. 1. The horizontal axis of FIG. 1 represents the ratio of Pd initially contained in the aqueous solution (2) (the value of the above-defined y expressed in percentage). The vertical axis of FIG. 1 represents the proportion of Pd measured by energy dispersive X-ray analysis (EDX). As shown in FIG. 1, the composition ratio of the Pd—Ru alloy fine particles formed was approximately equal to the ratio between the materials initially contained in the aqueous solution (2). Hereinafter, therefore, the molar ratio between $K_2[PdCl_4]$ and $RuCl_3 \cdot nH_2O$ dissolved in the aqueous solution (2) may be presented as the composition ratio of the Pd—Ru alloy fine particles.

Figure 2:
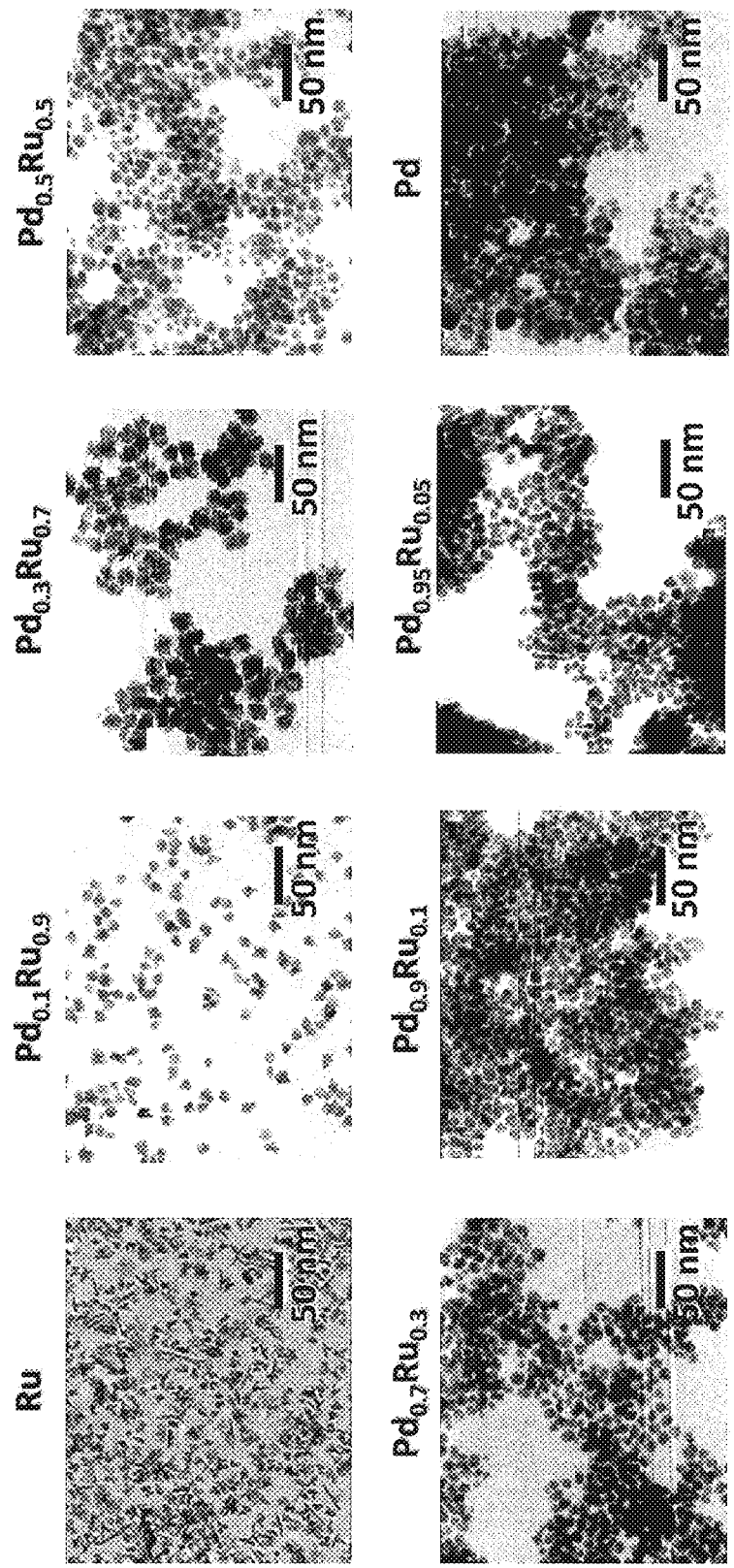
FIG. 2 shows TEM images of Pd—Ru alloy fine particles fabricated in an example.

Transmission electron microscope images (TEM images) of the obtained alloy fine particles are shown in FIG. 2. Also, the average particle diameters calculated based on the TEM images are shown in Table 1. The average particle diameter was determined by actually measuring the particle diameters (longitudinal diameters) of (at least 300) particles in the TEM image and calculating the average of the diameters. In the notation A±B nm, A represents the average particle diameter, and B represents the standard deviation.

TABLE 1

| | Ru | $Pd_{0.1}$—$Ru_{0.9}$ | $Pd_{0.3}$—$Ru_{0.7}$ | $Pd_{0.5}$—$Ru_{0.5}$ | $Pd_{0.7}$—$Ru_{0.3}$ | $Pd_{0.9}$—$Ru_{0.1}$ | $Pd_{0.95}$—$Ru_{0.05}$ | Pd |
|---|---|---|---|---|---|---|---|---|
| Average particle diameter (nm) | 6.4 ± 1.7 | 9.4 ± 1.7 | 10.4 ± 1.8 | 10.0 ± 1.2 | 8.2 ± 1.6 | 8.6 ± 1.4 | 9.2 ± 1.9 | 8.4 ± 1.7 |

(Element Mapping and Linear Analysis)

Figure 3A:
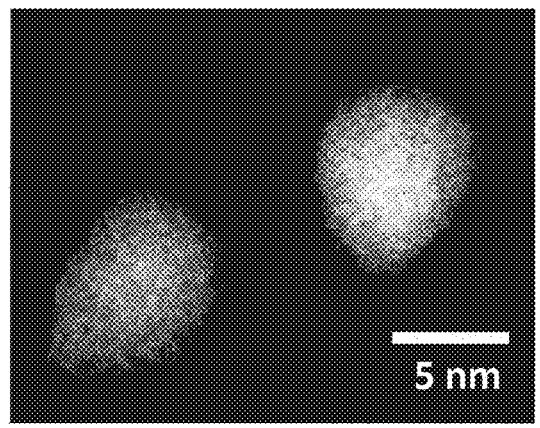
FIG. 3A shows a HAADF-STEM image of $Pd_{0.5}$—$Ru_{0.5}$ alloy fine particles produced in an example.
Figure 3B:
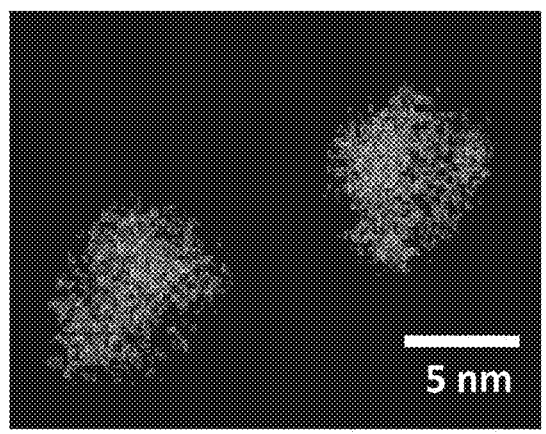
FIG. 3B shows a result of element mapping of Ru for $Pd_{0.5}$—$Ru_{0.5}$ alloy fine particles produced in an example.
Figure 3C:
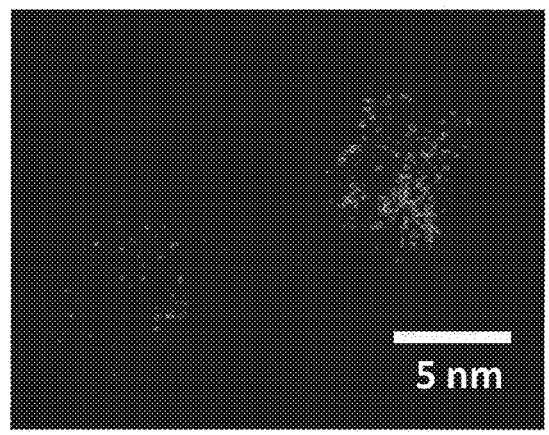
FIG. 3C shows a result of element mapping of Pd for $Pd_{0.5}$—$Ru_{0.5}$ alloy fine particles produced in an example.
Figure 3D:
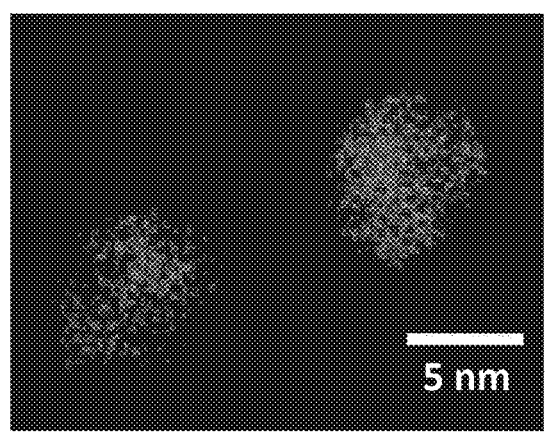
FIG. 3D shows a result of element mapping of Ru+Pd for $Pd_{0.5}$—$Ru_{0.5}$ alloy fine particles produced in an example.
Figure 4:
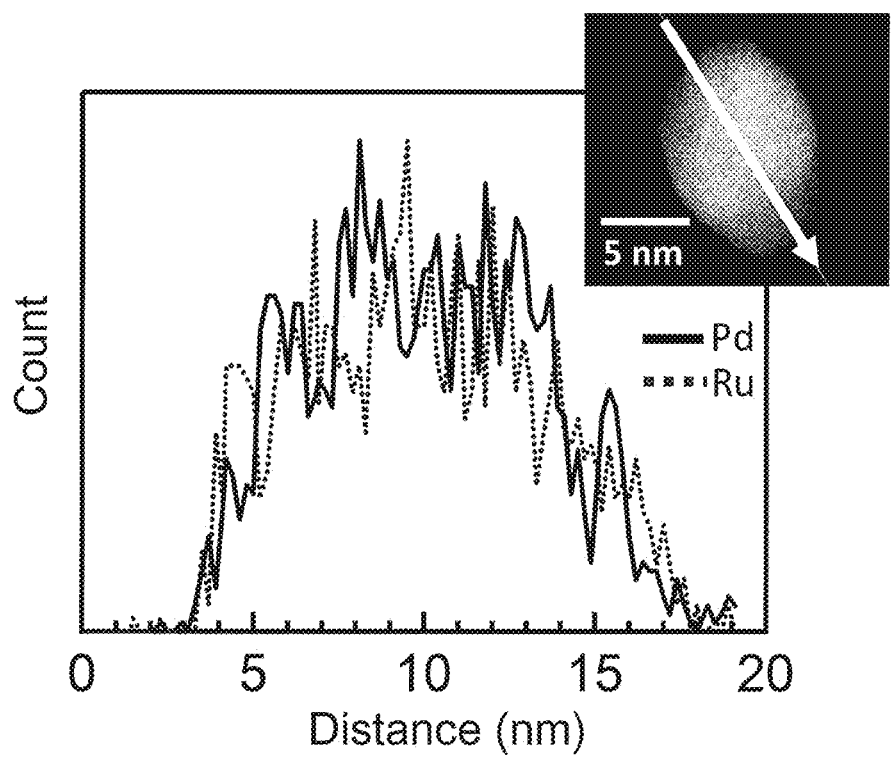
FIG. 4 shows a result of linear analysis for $Pd_{0.5}$—$Ru_{0.5}$ alloy fine particles produced in an example.
Figure 5A:
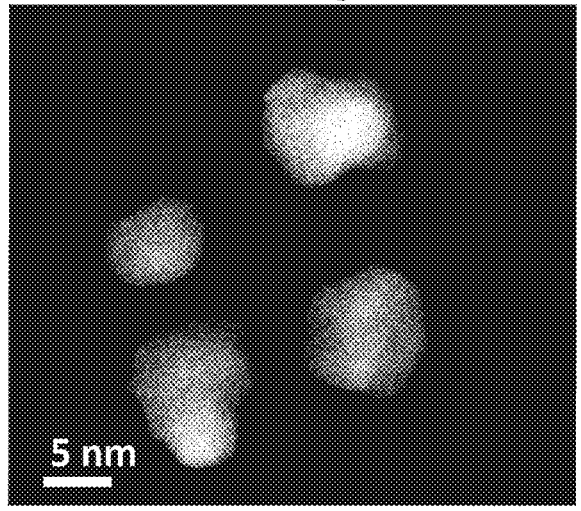
FIG. 5A shows a HAADF-STEM image of $Pd_{0.1}$—$Ru_{0.9}$ alloy fine particles produced in an example.
Figure 5B:
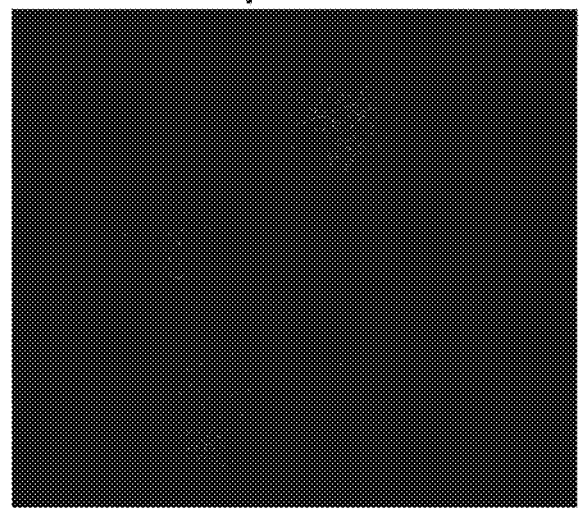
FIG. 5B shows a result of element mapping of Ru for $Pd_{0.1}$—$Ru_{0.9}$ alloy fine particles produced in an example.
Figure 5C:
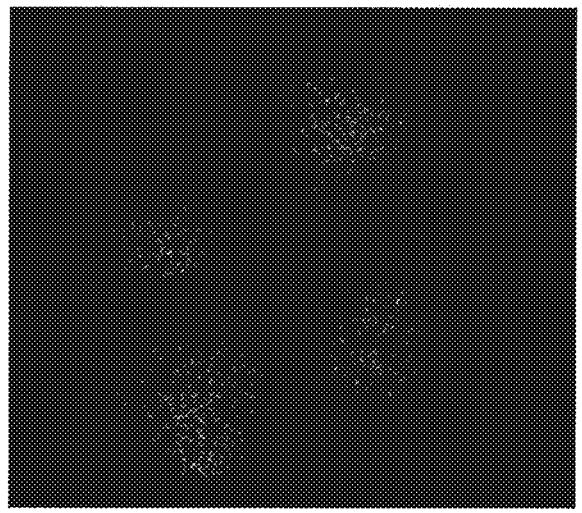
FIG. 5C shows a result of element mapping of Pd for $Pd_{0.1}$—$Ru_{0.9}$ alloy fine particles produced in an example.
Figure 5D:
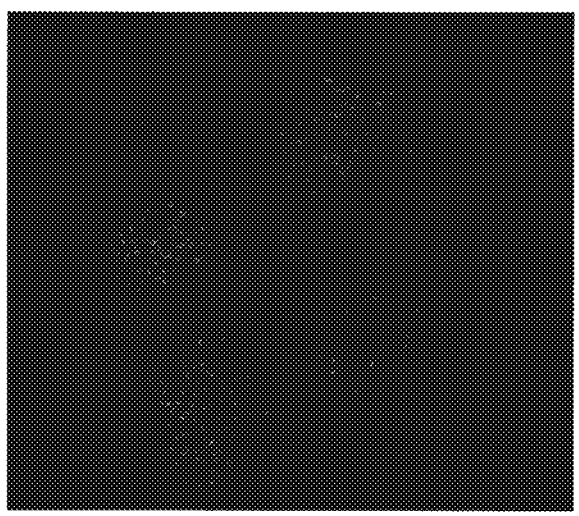
FIG. 5D shows a result of element mapping of Ru+Pd for $Pd_{0.1}$—$Ru_{0.9}$ alloy fine particles produced in an example.
Figure 6A:
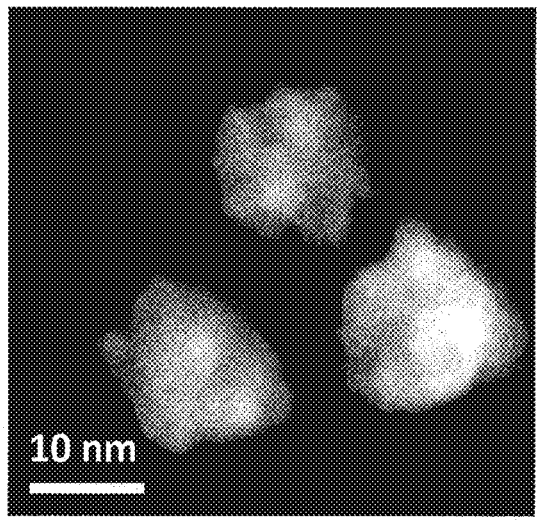
FIG. 6A shows a HAADF-STEM image of $Pd_{0.3}$—$Ru_{0.7}$ alloy fine particles produced in an example.
Figure 6B:
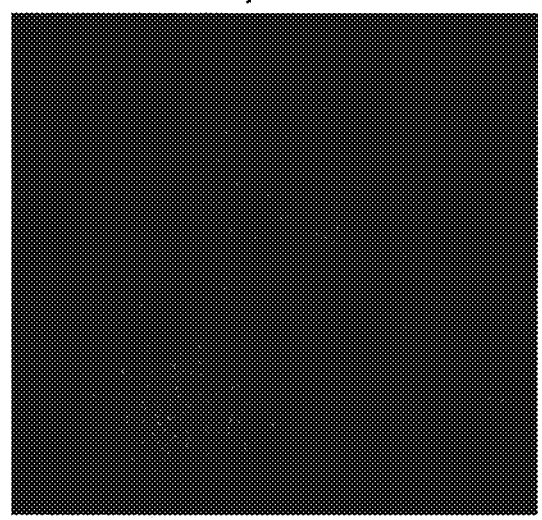
FIG. 6B shows a result of element mapping of Ru for $Pd_{0.3}$—$Ru_{0.7}$ alloy fine particles produced in an example.
Figure 6C:
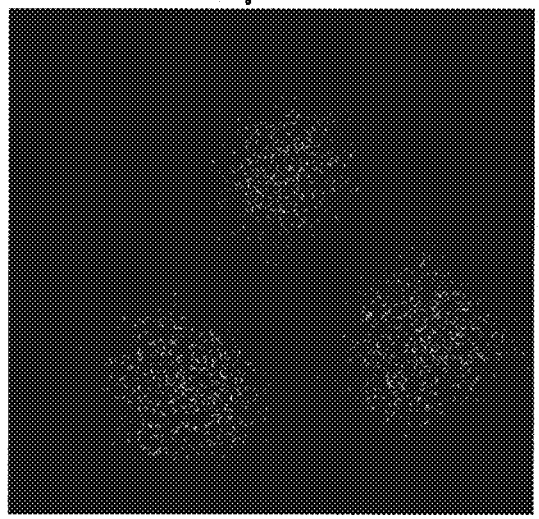
FIG. 6C shows a result of element mapping of Pd for $Pd_{0.3}$—$Ru_{0.7}$ alloy fine particles produced in an example.
Figure 6D:
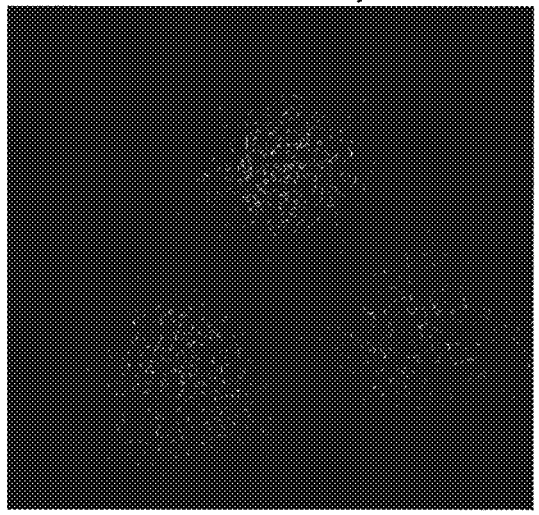
FIG. 6D shows a result of element mapping of Ru+Pd for $Pd_{0.3}$—$Ru_{0.7}$ alloy fine particles produced in an example.
Figure 7A:
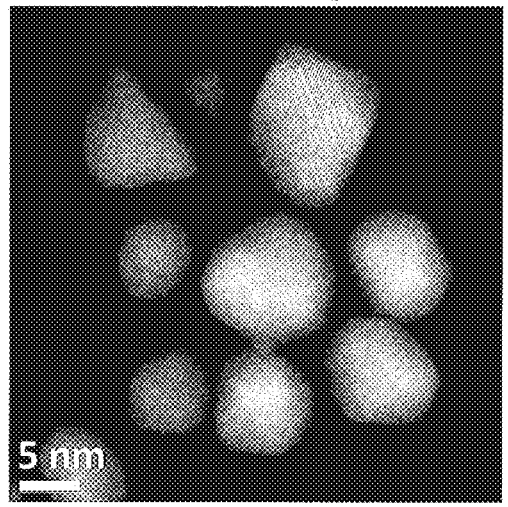
FIG. 7A shows a HAADF-STEM image of $Pd_{0.7}$—$Ru_{0.3}$ alloy fine particles produced in an example.
Figure 7B:
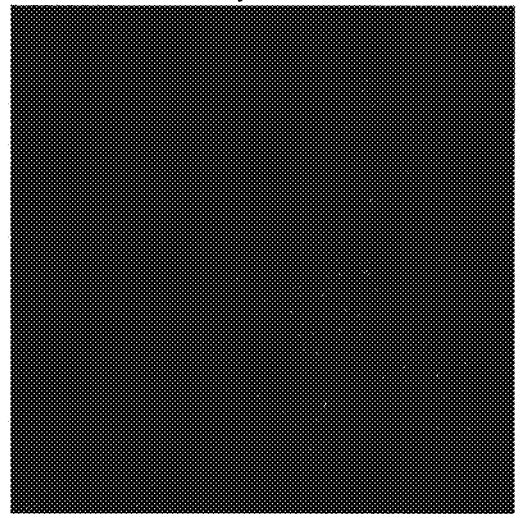
FIG. 7B shows a result of element mapping of Ru for $Pd_{0.7}$—$Ru_{0.3}$ alloy fine particles produced in an example.
Figure 7C:
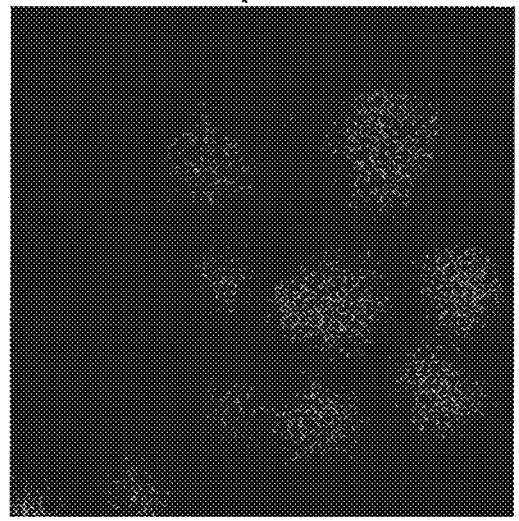
FIG. 7C shows a result of element mapping of Pd for $Pd_{0.7}$—$Ru_{0.3}$ alloy fine particles produced in an example.
Figure 7D:
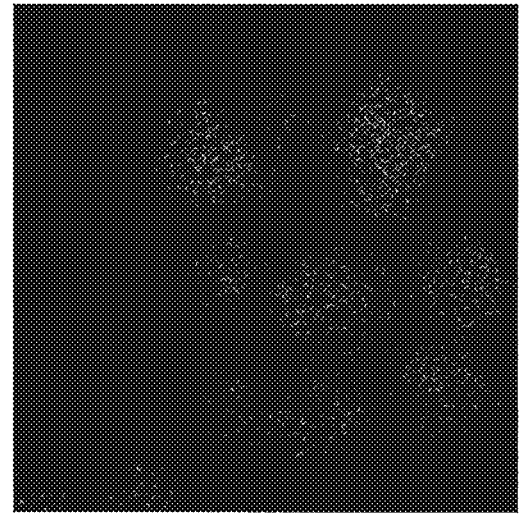
FIG. 7D shows a result of element mapping of Ru+Pd for $Pd_{0.7}$—$Ru_{0.3}$ alloy fine particles produced in an example.
Figure 8A:
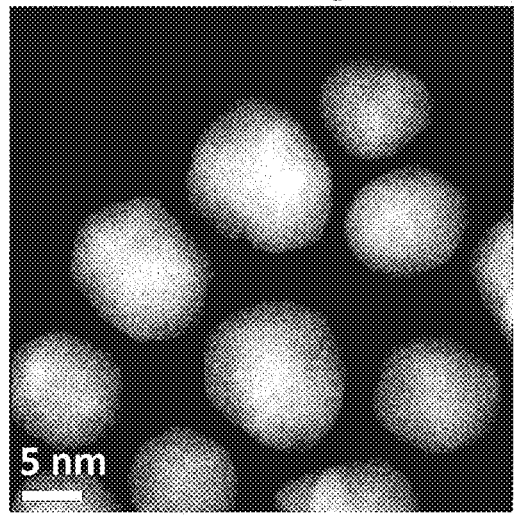
FIG. 8A shows a HAADF-STEM image of $Pd_{0.9}$—$Ru_{0.1}$ alloy fine particles produced in an example.
Figure 8B:
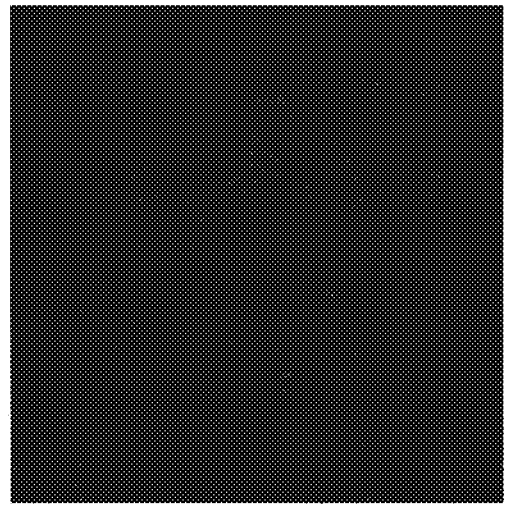
FIG. 8B shows a result of element mapping of Ru for $Pd_{0.9}$—$Ru_{0.1}$ alloy fine particles produced in an example.
Figure 8C:
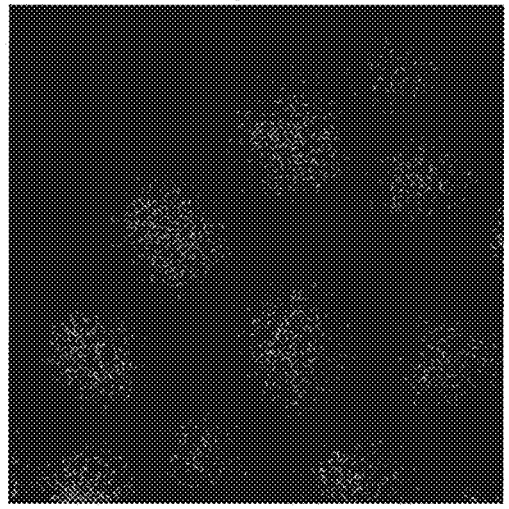
FIG. 8C shows a result of element mapping of Pd for $Pd_{0.9}$—$Ru_{0.1}$ alloy fine particles produced in an example.
Figure 8D:
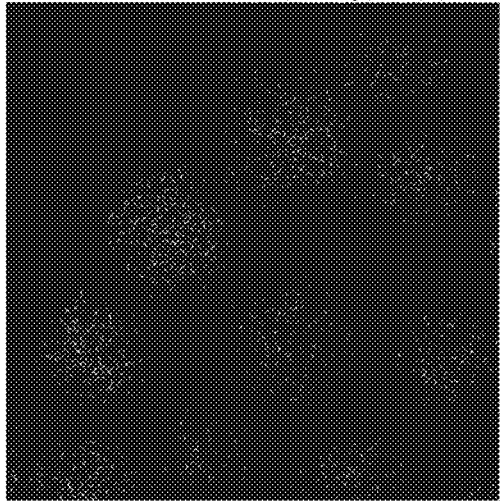
FIG. 8D shows a result of element mapping of Ru+Pd for $Pd_{0.9}$—$Ru_{0.1}$ alloy fine particles produced in an example.

Element mapping and linear analysis by energy dispersive X-ray analysis (EDX) were performed on the $Pd_{0.5}$—$Ru_{0.5}$ alloy fine particles obtained in the manner described above. Images taken by HAADF-STEM (High-Angle Annular Dark-Field Scanning Transmission Electron Microscopy) and results of the element mapping are shown in FIG. 3A to FIG. 3D. FIG. 3A shows a HAADF-STEM image. FIG. 3B, FIG. 3C, and FIG. 3D show the data of element mapping of Ru, Pd, and Ru+Pd, respectively. Also, results of the linear analysis are shown in FIG. 4.

The distribution of Ru in FIG. 3B and the distribution of Pd in FIG. 3C are both uniform over the whole particle. That is, FIG. 3A to FIG. 3D show that Ru and Pd are not in the separated phase, and both of the elements are uniformly distributed over the whole particle. FIG. 4A to FIG. 4D show the same results. That is, the data in FIG. 3A to FIG. 3D and FIG. 4 show that Pd and Ru form a solid solution at an atomic level in the $Pd_{0.5}$—$Ru_{0.5}$ alloy fine particles.

Results of element mapping on the $Pd_{0.1}$—$Ru_{0.9}$ alloy fine particles, $Pd_{0.3}$—$Ru_{0.7}$ alloy fine particles, $Pd_{0.7}$—$Ru_{0.3}$ alloy fine particles, and $Pd_{0.9}$—$Ru_{0.1}$ alloy fine particles are shown in FIG. 5A to FIG. 8D. FIG. 5A, FIG. 6A, FIG. 7A, and FIG. 8A show HAADF-STEM images. FIG. 5B, FIG. 6B, FIG. 7B, and FIG. 8B show the data of element mapping of Ru. FIG. 5C, FIG. 6C, FIG. 7C, and FIG. 8C show the data of element mapping of Pd. FIG. 5D, FIG. 6D, FIG. 7D, and FIG. 8D show the data of element mapping of Ru+Pd. In any of these cases, Pd and Ru were not in the separated phase in one particle, and both of the elements were uniformly distributed over the whole particle. These results indicate that Pd—Ru solid solution alloy fine particles were formed irrespective of the changes in composition.

Figure 9A:
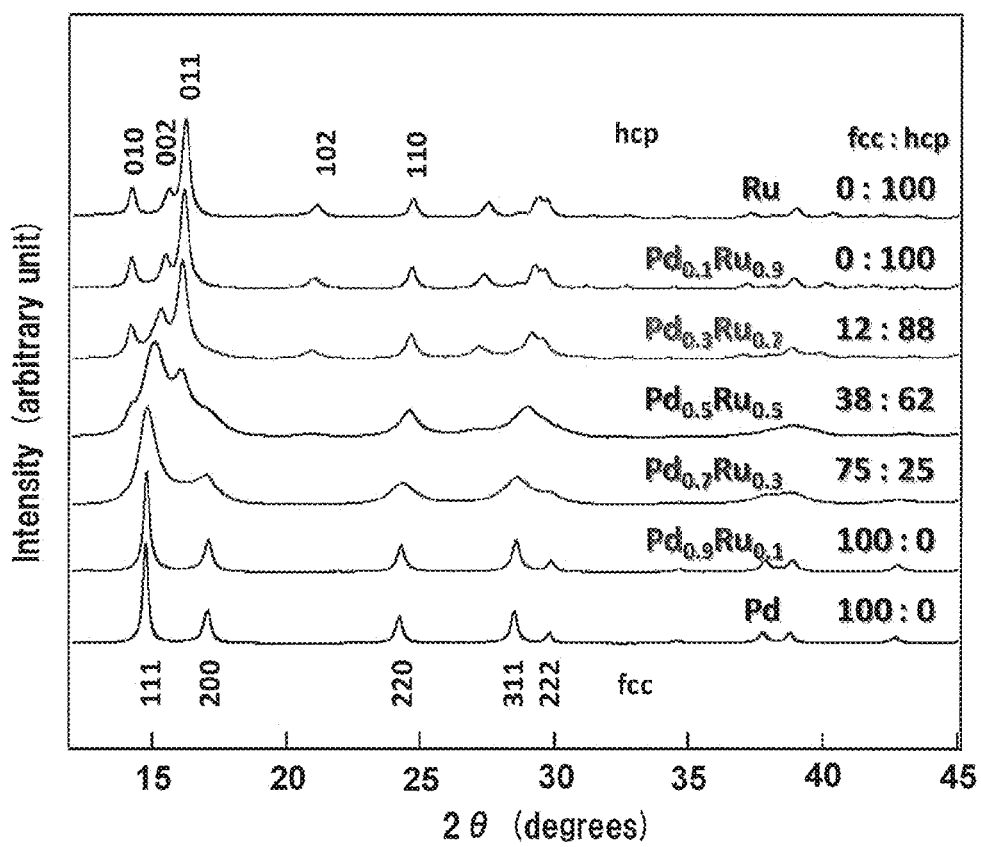
FIG. 9A shows XRD patterns of Pd—Ru alloy fine particles fabricated in an example.

An X-ray diffraction pattern (XRD pattern) of the $Pd_{0.5}$—$Ru_{0.5}$ alloy fine particles described above is shown in FIG. 9A. The ratios between crystal structures shown in FIG. 9A were calculated from the measured XRD pattern by Rietveld analysis. As shown in FIG. 9A, the peaks of the XRD pattern shifted with changes in composition.

Ru fine particles have a hcp structure, and Pd nanoparticles have a fcc structure. The XRD patterns show that the structure of the Pd—Ru alloy fine particles changes from a hcp structure to a fcc structure with increase in the proportion of Pd. That is, as the proportion of Pd increases, the proportion of the hcp structure decreases, and the proportion of the fcc structure increases.

Figure 9B:
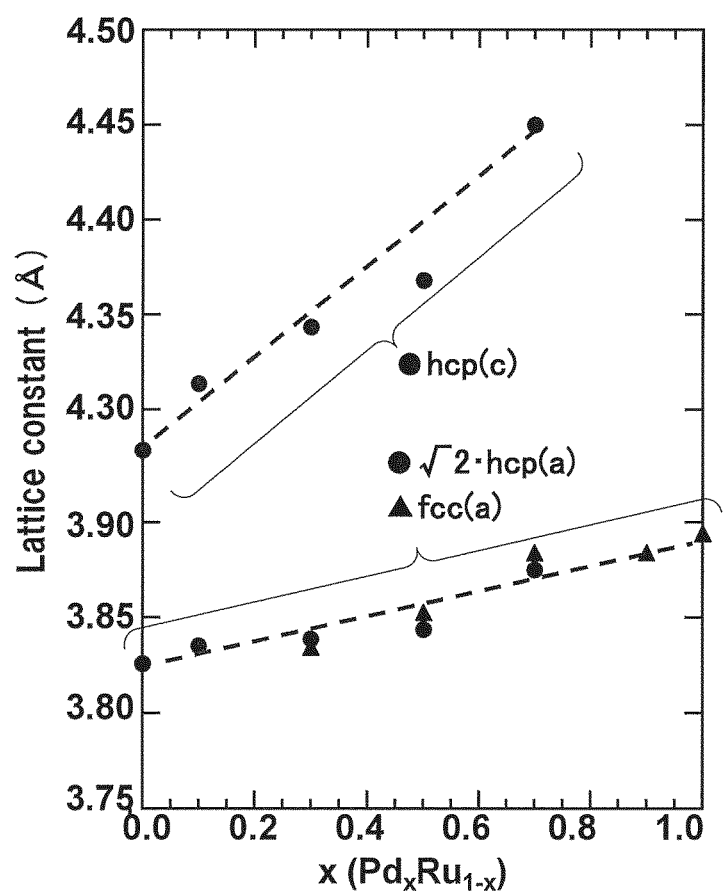
FIG. 9B shows the relationship between the composition ratio and the lattice constants in Pd—Ru alloy fine particles fabricated in an example.

The hcp structure and the fcc structure are both closest packing structures. When the interatomic distances are equal for the two structures, a value obtained by multiplying the a-axis lattice constant of the hcp structure by $2^{1/2}$ (the square root of 2) is equal to the a-axis lattice constant of the fcc structure. In view of this, the relationship between the composition ratio and the lattice constants was determined from the XRD patterns of FIG. 9A. FIG. 9B shows the relationships between the composition ratio and the value obtained by multiplying the a-axis lattice constant of the hcp structure by $2^{1/2}$ (the square root of 2), between the composition ratio and the c-axis lattice constant of the hcp structure, and between the composition ratio and the a-axis lattice constant of the fcc structure.

As shown in FIG. 9A, in Pd—Ru alloy fine particles in which the proportion of Pd is in the range of 30 atomic % to 70 atomic %, the fcc structure and the hcp structure coexist. Meanwhile, as shown in FIG. 9B, the average interatomic distance in the fcc structure and the average interatomic distance in the hcp structure were approximately equal. This indicates that the fcc structure portion and the hcp structure portion in the Pd—Ru alloy fine particles are solid solutions differing in crystal structure but having approximately equal composition ratios. In addition, the lattice constants change approximately linearly with changes in composition. These facts indicate that both the hcp structure and the fcc structure coexisting in each of the alloy fine particles are in the form of a solid solution having a composition ratio approximately equal to the ratio between the materials initially contained in the solution.

As described above, the experimental data demonstrated that, in the Pd—Ru alloy fine particles fabricated, Pd and Ru were not in the separated phases of a fcc structure and a hcp structure, respectively, and Pd and Ru formed a solid solution in each of the fcc structure and the hcp structure.

Figure 10:
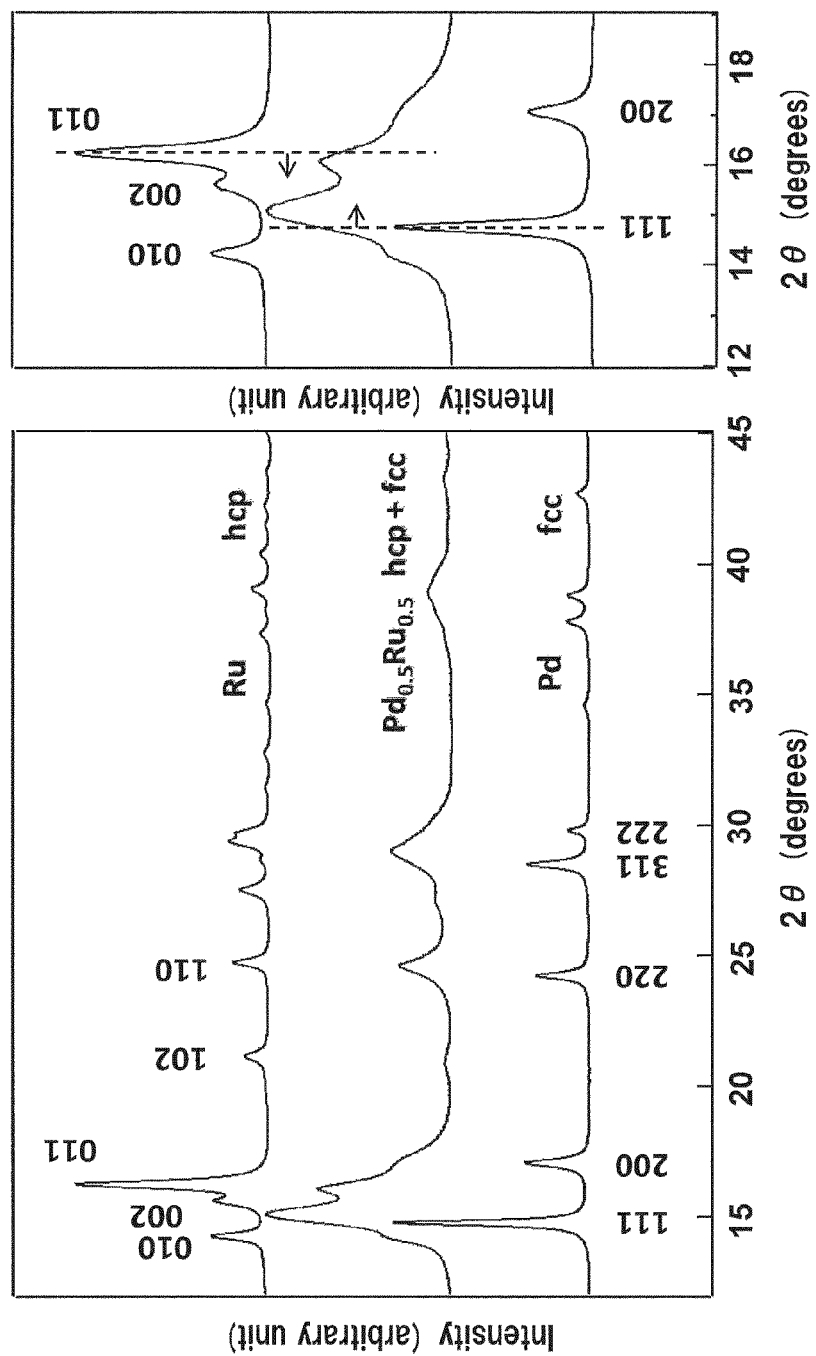
FIG. 10 shows an XRD pattern of $Pd_{0.5}$—$Ru_{0.5}$ alloy fine particles produced in an example.

An XRD pattern of the $Pd_{0.5}$—$Ru_{0.5}$ alloy fine particles is shown in FIG. 10. In FIG. 10, XRD patterns of Pd (fcc structure) and Ru (hcp structure) are also shown. As shown in the partially-enlarged diagram of FIG. 10, the diffraction peaks of the $Pd_{0.5}$—$Ru_{0.5}$ alloy fine particles are shifted from the diffraction peaks of the fcc structure and the hcp structure. This data, similarly to the above-described data, suggests that solid solution alloy fine particles were formed.

Figure 11:
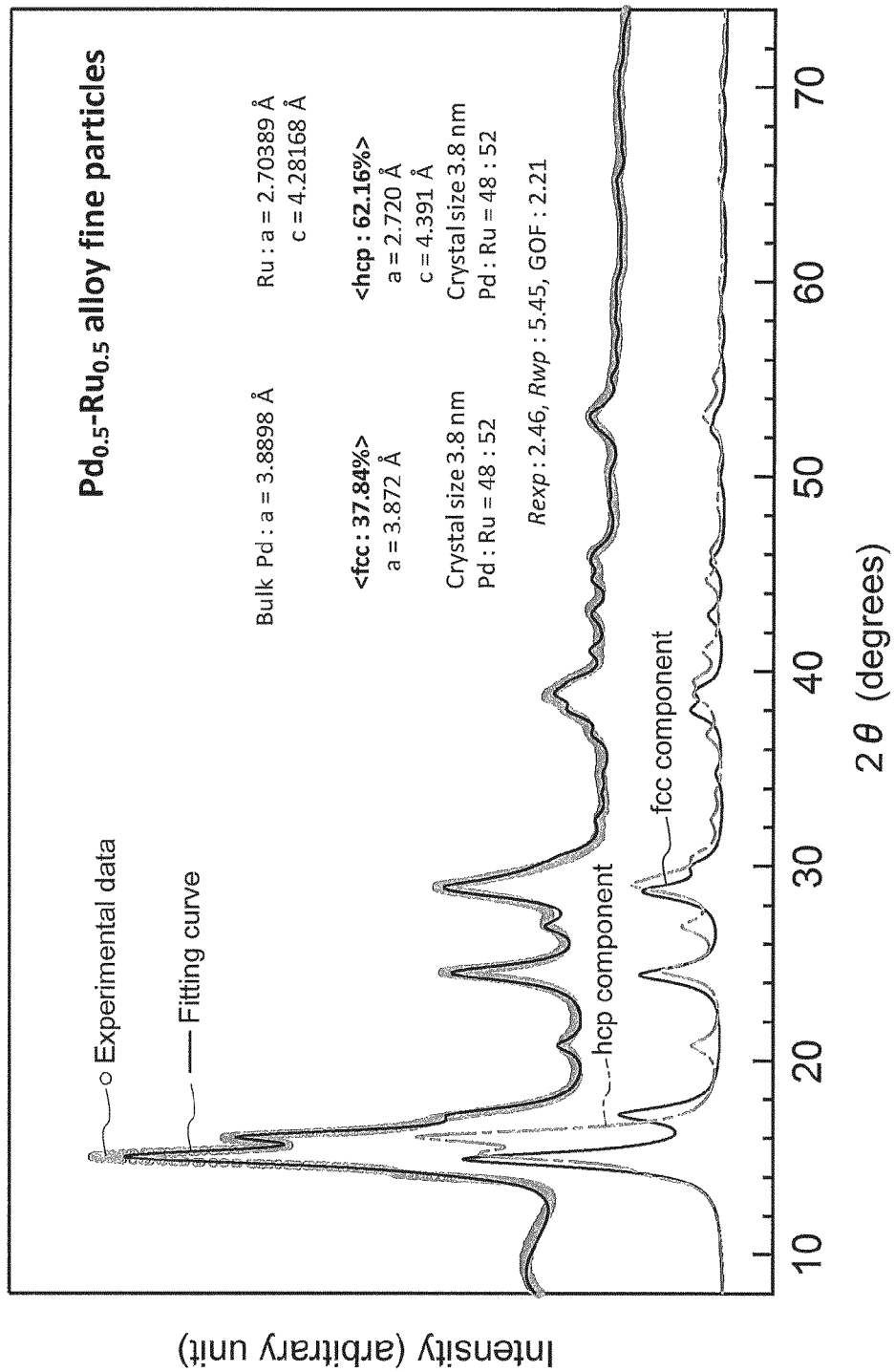
FIG. 11 shows a result of fitting of an XRD pattern of $Pd_{0.5}$—$Ru_{0.5}$ alloy fine particles fabricated in an example.

A result of Rietveld analysis of the $Pd_{0.5}$—$Ru_{0.5}$ alloy fine particles is shown in FIG. 11. For the XRD pattern of the $Pd_{0.5}$—$Ru_{0.5}$ alloy fine particles, fitting was performed using two components attributed to the fcc structure and the hcp structure. The difference in atomic number (electron number) between Pd and Ru is only two; for this reason, they cannot be differentiated based on the diffraction intensities of the XRD patterns. Therefore, in the performed analysis, the metal composition ratio in the atomic arrangement of the initial form of each of the two structures was fixed at a metal composition ratio obtained by EDX.

The calculated lattice constant of the fcc component (a=3.872 angstrom) was smaller than the lattice constant of Pd in the form of a bulk (a=3.8898 angstrom). In addition, the calculated lattice constants of the hcp component (a=2.720 angstrom, c=4.391 angstrom) were larger than the lattice constants of Ru in the form of a bulk (a=2.70389 angstrom, c=4.28168 angstrom). These facts indicate that the $Pd_{0.5}$—$Ru_{0.5}$ alloy fine particles are solid solution alloy fine particles. The abundance ratio between the fcc structure and the hcp structure was calculated to be about 4:6.

Usually, Pd and Ru do not form a solid solution at almost any composition ratio. However, with the production method of the present invention, Pd—Ru solid solution alloy fine particles were obtained as described above. One reason for this is that the production method has a special feature. Another possible reason is that the Pd—Ru alloy fine particles produced have a nanometer-order diameter, and have properties different from those of bulks.

Example 1

Catalytic Activity for Oxidation Reaction of Carbon Monoxide

The Pd—Ru alloy fine particles ($Pd_{0.5}$—$Ru_{0.5}$) fabricated by the above method were evaluated for their catalytic activity for oxidation reaction of carbon monoxide.

[Preparation of Catalyst]

A catalyst using the Pd—Ru alloy fine particles ($Pd_{0.5}$—$Ru_{0.5}$) was prepared by the following procedures. First, a given amount of the alloy fine particles having been dried was weighed out, put into purified water, and treated with ultrasonic wave, so that a dispersion of the alloy fine particles was obtained. At this time, the amount of the alloy fine particles weighed out was determined by calculation based on the content of each metal determined beforehand by element analysis. A γ-alumina powder (Japan Reference Catalyst JRC-ALO8) prebaked at 800° C. for 5 hours was added to this dispersion, which was stirred with a magnetic stirrer for 12 hours. The stirred liquid was transferred to a rotary evaporator, heated to 60° C. under reduced pressure, and then dried until a powder was yielded. Thereafter, the obtained powder was allowed to stand in a dryer at 120° C. for 8 hours in order to fully remove water from the powder. The dried powder was sufficiently pulverized with a mortar, and then formed into a disk shape by a uniaxial forming device under the conditions of 1.2 MPa and 5 minutes. The resulting formed product was crushed, and then sifted to obtain particles having diameters of 180 to 250 μm. In this manner, a noble metal-supported catalyst in which the $Pd_{0.5}$—$Ru_{0.5}$ alloy fine particles are supported (supported amount: 1 wt %) on a support (γ-alumina) was prepared.

For comparison, other noble metal-supported catalysts were prepared in the same manner as described above, except that other fine particles were used instead of the Pd—Ru alloy fine particles. As the fine particles substituting for the Pd—Ru alloy fine particles, Ru fine particles, Rh fine particles, Pd fine particles, and a physical mixture of Ru fine particles and Pd fine particles were used.

[Activity Measurement]

The catalytic activity for CO oxidation reaction was measured using a fixed-bed flow reactor. First, 75 mg of the catalyst formed into pellets was loaded in a quartz reaction tube with an inner diameter of 7 mm by means of quartz wool. The feed of a mixed gas of He, CO, and $O_2$ (He/CO/$O_2$=49/0.5/0.5 ml·min$^{-1}$) into this reaction tube was started at room temperature, and then the catalyst layer was heated to 100° C. A gas was collected thorough the outlet of the reaction tube 15 minutes after the temperature of the catalyst layer reached 100° C. The reaction product was analyzed using a gas chromatograph equipped with a thermal conductivity detector. After completion of the analysis, the temperature of the catalyst layer was increased by 10° C. and then, after 15 minutes, the product was analyzed again. With repetitions of this operation, the temperature of the catalyst layer was increased until CO was completely consumed. After completion of the experiment, the reaction tube was left to cool to room temperature while being purged with He. Then, the catalyst was taken out.

Additionally, catalysts were prepared using Pd—Ru alloy fine particles having compositions represented by $Pd_{0.3}$—$Ru_{0.7}$, $Pd_{0.7}$—$Ru_{0.3}$, $Pd_{0.1}$—$Ru_{0.9}$, and $Pd_{0.9}$—$Ru_{0.1}$ in the same manner as described above, and their CO oxidation activities were measured in the same manner as described above.

Figure 12:
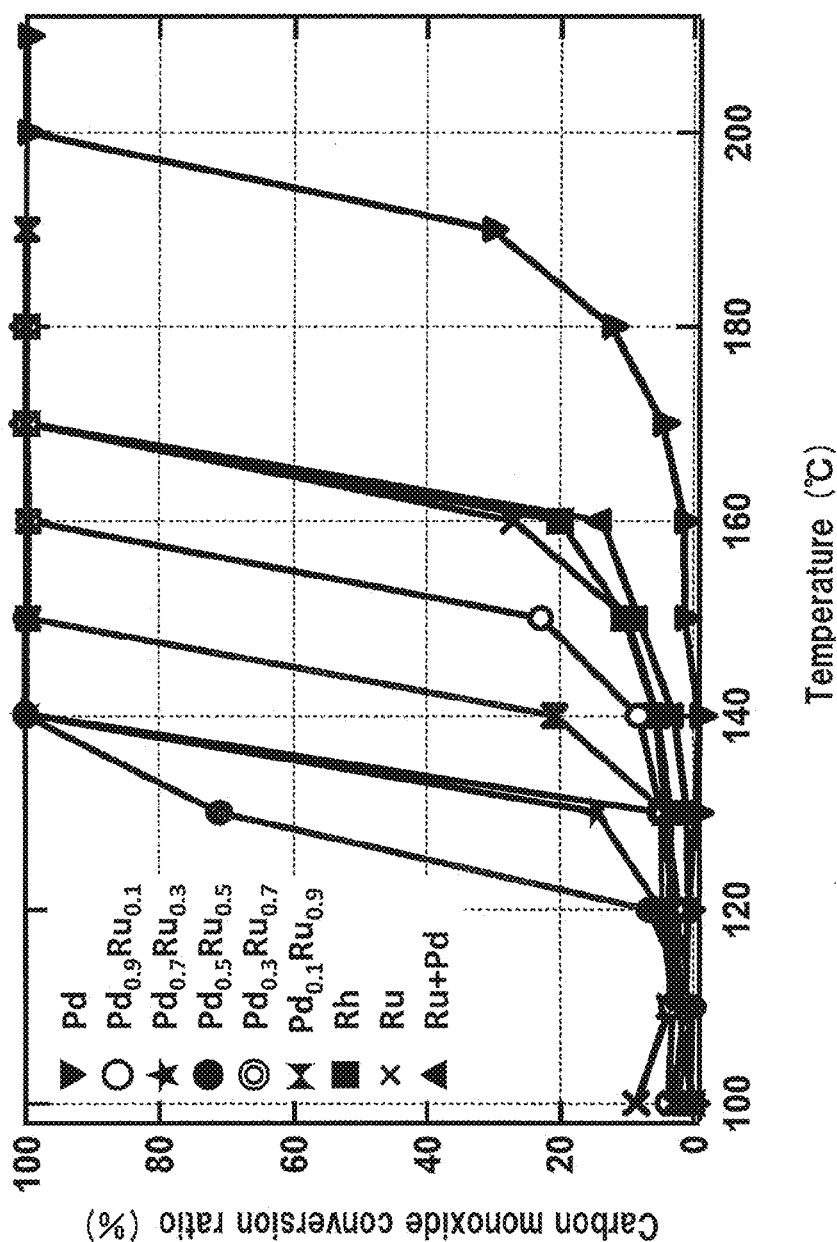
FIG. 12 is a graph showing the catalytic activities of Pd—Ru alloy fine particles fabricated in an example and other fine particles for oxidation reaction of carbon monoxide.

The measurement results are shown in FIG. 12. FIG. 12 shows the proportion of carbon monoxide converted to carbon dioxide. As shown in FIG. 12, the Pd—Ru alloy fine particles exhibited the highest catalytic activities. The catalytic activity of the alloy fine particles in which Pd:Ru was 1:1 was highest. For the results of FIG. 12, it is noteworthy that the catalytic activities of the Pd—Ru alloy fine particles were higher than the catalytic activity of any of Pd fine particles, Ru fine particles, Rh fine particles, and a mixture of Pd fine particles and Ru fine particles. This suggests that the Pd—Ru solid solution alloy fine particles exhibit properties different from those of Pd alone or Ru alone. Therefore, the Pd—Ru solid solution alloy fine particles are expected to be used in a variety of non-conventional applications; for example, they are expected to be used as a catalyst for a variety of reactions.

Example 2

Catalytic Activity for Reduction Reaction of Nitrogen Oxide

Noble metal-supported catalysts using $Pd_{0.5}$—$Ru_{0.5}$ alloy fine particles, $Pd_{0.1}$—$Ru_{0.9}$ alloy fine particles, or $Pd_{0.9}$—$Ru_{0.1}$ alloy fine particles were fabricated in the same manner as described above, and their catalytic activities for reduction reaction of nitrogen oxide ($NO_X$) were evaluated. For comparison, other noble metal-supported catalysts were prepared in the same manner as described above, except that other fine particles were used instead of the Pd—Ru alloy fine particles. As the fine particles substituting for the Pd—Ru alloy fine particles, Ru fine particles, Pd fine particles, and a physical mixture of Ru fine particles and Pd fine particles were used.

The evaluation of the catalytic activity for $NO_X$ reduction reaction was performed using a fixed-bed flow reactor. Specifically, first, 200 mg of the catalyst formed into pellets was loaded in a quartz reaction tube with an inner diameter of 7 mm by means of quartz wool. This reaction tube was connected to the reactor, and then the reaction tube was purged with He gas sufficiently. Under the flow of He gas, the temperature of the catalyst layer was increased up to 150° C. at a rate of 10° C./minute. After confirming that the temperature of the catalyst layer was stabilized at 150° C., a mixed gas of $NO_X$, $O_2$, $CO_2$, CO, $C_3H_6$, and $N_2$ ($NO_X$: 260 ppm, $O_2$: 0.51%, $CO_2$: 6.0%, CO: 1.0%, $C_3H_6$: 1330 ppm, $N_2$: balance gas) was fed at a flow rate adjusted so that the space velocity was 60,000 ml/(h·$g_{cat}$). The time at this moment was set as the reaction initiation time. Furthermore, 30 minutes after the start of the feed of the mixed gas, the reaction temperature was increased up to 200° C. at a rate of 10° C./minute, and maintained at 200° C. for 30 minutes. Subsequently, the operation of increasing the temperature by 50° C. and maintaining the increased temperature for 30 minutes was repeated until the reaction temperature reached 300° C. Along with the series of temperature changes, the concentrations of NO and $NO_2$ in the gas output through the catalyst layer were continuously analyzed by a $NO_X$ analyzer to evaluate the temperature dependence of the catalytic activity for $NO_X$ reduction reaction.

Figure 13:
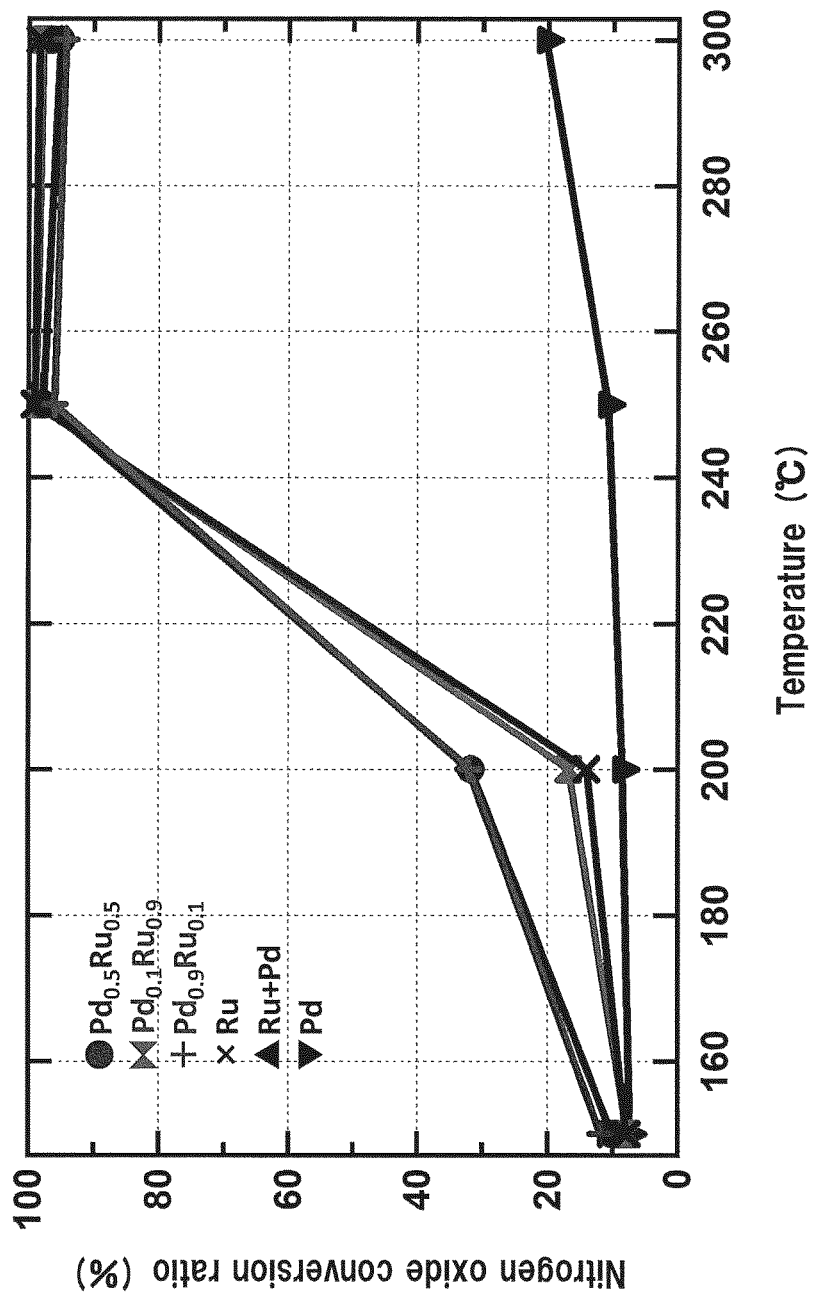
FIG. 13 is a graph showing the catalytic activities of Pd—Ru alloy fine particles fabricated in an example and other fine particles for reduction reaction of nitrogen oxide.

The evaluation results are shown in FIG. 13. The vertical axis of FIG. 13 represents the proportion of nitrogen oxide having been converted. As shown in FIG. 13, an increase in catalytic activity resulting from forming Pd and Ru into a solid solution alloy was observed for every composition. It can be thought from the results of FIG. 13 that the catalytic activity is highest when Pd:Ru is in the range of 0.1:0.9 to 0.9:0.1.

Example 3

Catalytic Activity for Oxidation Reaction of Hydrogen Gas

A noble metal-supported catalyst using Pd—Ru alloy fine particles ($Pd_{0.5}$—$Ru_{0.5}$) was fabricated in the same manner as described above, and its catalytic activity for oxidation reaction of hydrogen gas was evaluated. For comparison, other noble metal-supported catalysts were fabricated in the same manner as described above, except that other fine particles were used instead of the Pd—Ru alloy fine particles. As the fine particles substituting for the Pd—Ru alloy fine particles, Ru fine particles, Pd fine particles, and Rh fine particles were used. Additionally, another catalyst using Ru fine particles was fabricated by an impregnation process. Specifically, a Ru metal salt was supported onto alumina particles, which was followed by baking to fabricate a catalyst in which Ru fine particles were supported on the alumina particles.

The catalytic activity for oxidation reaction of hydrogen gas was evaluated using a fixed-bed flow reactor. Specifically, first, 50 mg of the catalyst formed into pellets was loaded in a quartz reaction tube with an inner diameter of 7 mm by means of quartz wool. This reaction tube was connected to the reactor, then the feed of a mixed gas of Ar, $H_2$, and $O_2$ (Ar/$H_2$/$O_2$=49/0.5/0.5 ml/min) was started at room temperature, and the catalyst was heated to 100° C. A gas was collected thorough the outlet of the reaction tube 15 minutes after the temperature of the catalyst reached 100° C., and the reaction product was analyzed using a gas chromatograph equipped with a thermal conductivity detector. After completion of the analysis, the temperature of the catalyst layer was increased by 25° C. and maintained for 15 minutes, after which the product was analyzed again. With repetitions of this operation, the temperature of the catalyst layer was increased until $H_2$ was completely consumed. After completion of the experiment, the reaction tube was left to cool to room temperature while being purged with Ar gas. Then, the catalyst was taken out.

Figure 14:
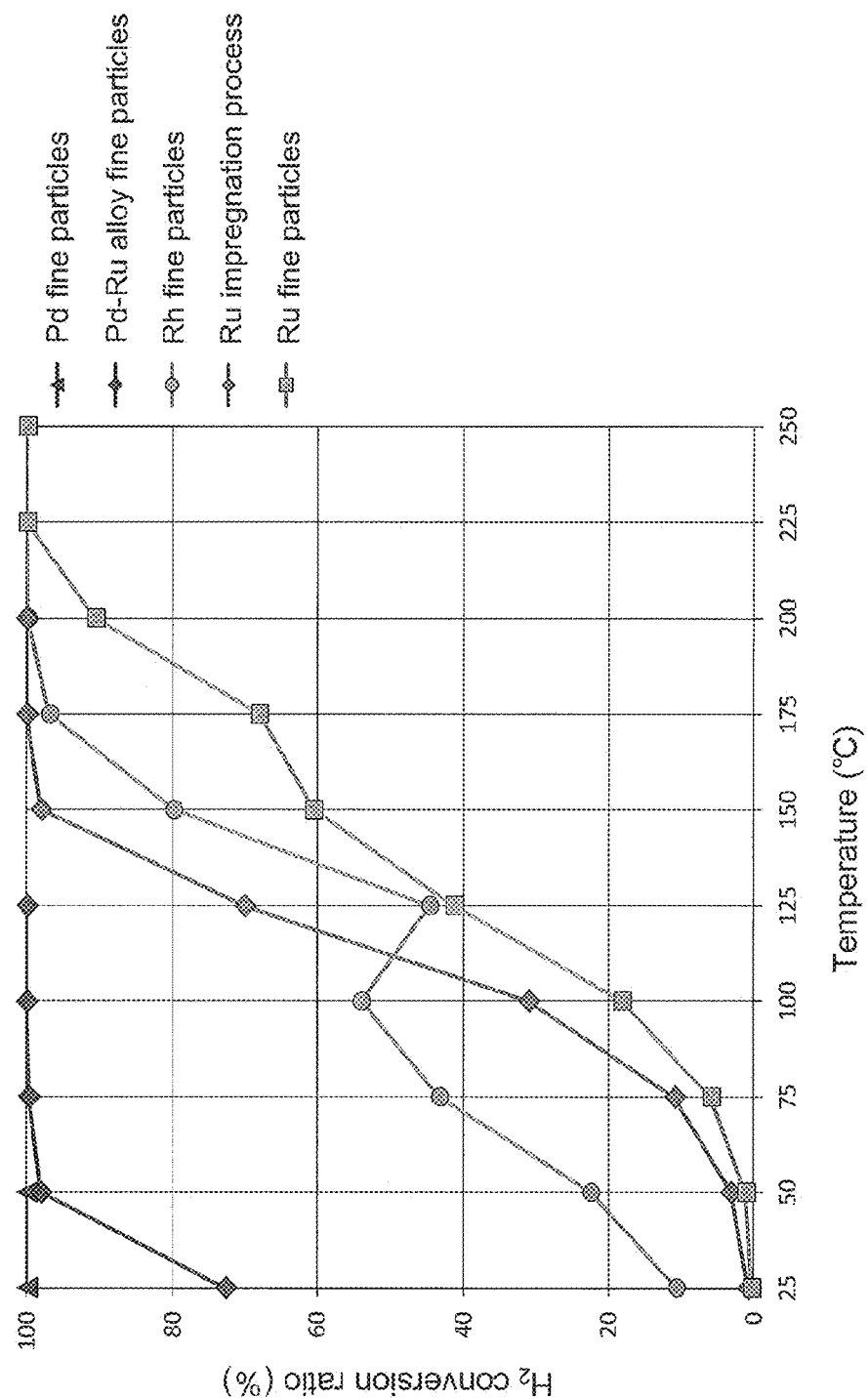
FIG. 14 is a graph showing the catalytic activities of Pd—Ru alloy fine particles fabricated in an example and other fine particles for oxidation reaction of hydrogen gas.

The evaluation results are shown in FIG. 14. The vertical axis of FIG. 14 represents the proportion of hydrogen gas having been oxidized. In FIG. 14, the evaluation results obtained when using other fine particles are also shown. The term "Ru impregnation process" in FIG. 14 means the process in which a Ru metal salt is supported onto alumina particles, followed by baking to allow Ru fine particles to be supported on the alumina particles. As shown in FIG. 14, the Pd—Ru alloy fine particles had the second highest catalytic activity after the Pd fine particles.

Example 4

Suzuki-Miyaura Cross-Coupling

In Example 4, the catalytic activity of Pd—Ru alloy fine particles ($Pd_{0.5}$—$Ru_{0.5}$) for Suzuki-Miyaura cross-coupling was evaluated using a plurality of bases. In the following examples, the alloy fine particles were used without being supported on a support.

First, Pd—Ru alloy fine particles ($Pd_{0.5}$—$Ru_{0.5}$) protected by PVP were fabricated from a Pd compound and a Ru compound by the above-described method. Next, the Pd—Ru alloy fine particles were put into a test tube, to which were sequentially added 4-methylphenylboronic acid (1.2 mmol), a solvent, bromobenzene (1.0 mmol), and a base (3 mmol). Then, the reaction was allowed to proceed at room temperature (26 to 27° C.) for 10 minutes. As the solvent, a mixed solvent of ethanol (3 mL) and water (3 mL) was used. The alloy fine particles were added in such an amount that the Pd and Ru contents were each 0.25 mol % (0.5 mol % in total) with respect to bromobenzene. The amount of the PVP added together with the alloy fine particles was 13.4 mass % as calculated by the formula PVP/(PVP+Metals).

In Example 4, the catalytic activity was examined using different bases. The reaction in Example 4 is shown below. The reaction product (3) is formed by a cross-coupling reaction between bromobenzene and 4-methylphenylboronic acid. The reaction product (4) is formed by a homocoupling reaction between the 4-metylphenylboronic acid molecules.

[Chemical formula 3]

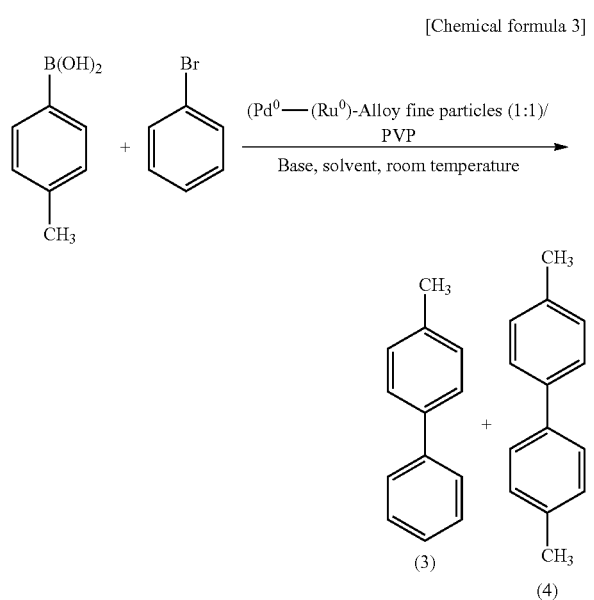

The evaluation results are shown in Table 2. The yields of the reaction products were determined by NMR. The yield of the product (3) formed by the cross-coupling reaction was determined with respect to the amount of one compound of the starting materials that was smaller in amount than the other (the amount of bromobenzene in the case of Example 4). The yield of the product formed by the homocoupling reaction was determined with respect to the amount of the compound used as the starting material (4-metylphenylboronic acid in the case of the product (4)). Accordingly, if the starting materials are fully consumed in the reactions, the total of the yield of the product formed by the cross-coupling reaction and the yield of the product formed by the homo-coupling reaction exceeds 100% (the same applies to the subsequent examples).

TABLE 2

| Base | Yield (%) | |
|---|---|---|
| | (3) Cross-coupling | (4) Homocoupling |
| $Na_2CO_3$ | 69.0 | 13.8 |

TABLE 2-continued

| Base | Yield (%) | |
|---|---|---|
| | (3) Cross-coupling | (4) Homocoupling |
| $K_2CO_3$ | 78.3 | 14.0 |
| $Rb_2CO_3$ | 54.1 | 16.7 |
| $Cs_2CO_3$ | 38.3 | 21.8 |
| $NaOCOCH_3$ | 4.0 | 37.1 |
| KSCN | 4.8 | 33.4 |
| $(NH_4)_2HPO_4$ | 0.0 | 37.0 |
| $Na_2HPO_4$ | 14.3 | 41.0 |
| Not used | 0.0 | 7.3 |

Under the above reaction conditions, as shown in Table 2, the yield of the cross-coupling was highest when $K_2CO_3$ was used as the base.

Example 5

In Example 5, the catalytic activity of Pd—Ru alloy fine particles ($Pd_{0.5}$—$Ru_{0.5}$) for Suzuki-Miyaura cross-coupling was evaluated at different reaction temperatures using different solvents. In Example 5, the reaction was performed under the conditions shown below. The procedures for the reaction were the same as those in Example 4.

Starting materials and their amounts: Same as those in Example 4
Catalyst and its amount: Same as those in Example 4
Solvent: Mixed solvent of ethanol (3 mL) and water (3 mL) or mixed solvent of N,N-dimethylacetamide (3 mL) and water (3 mL)
Base: $K_2CO_3$ (3 mmol)
Reaction temperature: As listed in Table 3
Reaction time: As listed in Table 3
The yields of the reaction products are shown in Table 3. Hereinafter, ethanol may be denoted by "EtOH", and N,N-dimethylacetamide may be denoted by "DMA".

TABLE 3

| Reaction temperature | Reaction time (minutes) | Solvent | Yield (%) | |
|---|---|---|---|---|
| | | | (3) Cross-coupling | (4) Homo-coupling |
| Room temperature | 10 | EtOH + Water | 78.3 | 14.0 |
| | | DMA + Water | 38.2 | 24.3 |
| 100° C. | 5 | EtOH + Water | 91.1 | 10.1 |
| | | DMA + Water | 100 | 8.2 |

As shown in Table 3, the yield of the cross-coupling was highest when the mixed solvent of DMA and water was used as the solvent and the reaction temperature was 100° C. Regardless of which solvent was used, the yield of the cross-coupling was higher when the reaction temperature was 100° C. However, in the case of using the mixed solvent of ethanol and water, the decrease in the yield of the cross-coupling was small even when the reaction was performed at room temperature.

Example 6

In Example 6, the catalytic activity of Pd—Ru alloy fine particles for Suzuki-Miyaura cross-coupling was evaluated for different alloy compositions. In Example 6, the reaction was performed under the conditions shown below. The procedures for the reaction were the same as those in Example 4. As the catalysts, $Pd_{0.5}$—$Ru_{0.5}$ alloy fine particles, $Pd_{0.1}$—$Ru_{0.9}$ alloy fine particles, and $Pd_{0.9}$—$Ru_{0.1}$ alloy fine particles were used. These were fine particles fabricated by the method described above and were protected by PVP.

Starting materials and their amounts: Same as those in Example 4

Amounts of catalyst and PVP: As listed in Table 4

Solvent: Mixed solvent of ethanol (3 mL) and water (3 mL)

Base: $K_2CO_3$ (3 mmol)

Reaction temperature: Room temperature

Reaction time: 10 minutes

As comparative examples, similar evaluations were made using Pd fine particles and Ru fine particles instead of the alloy fine particles. Some of the reaction conditions and the evaluation results are shown in Table 4.

TABLE 4

| Catalyst No. (Pd:Ru ratio) | PVP (mass %) | Pd (mol %) | Ru (mol %) | Yield | | |
|---|---|---|---|---|---|---|
| | | | | (3) Cross-coupling (%) | (4) Homocoupling (%) | Total (%) |
| 4-1 Pd/PVP (1:0) | 13.7 | 0.25 | 0 | 30.1 | 23.1 | 53.2 |
| 4-2 Ru/PVP (0:1) | 13.8 | 0 | 0.25 | 3.5 | 30.8 | 34.3 |
| 4-3 Pd—Ru/PVP (1:1) | 13.4 | 0.25 | 0.25 | 78.3 | 14.0 | 92.3 |
| 4-4 Pd—Ru/PVP (1:1) | 13.4 | 0.125 | 0.125 | 47.3 | 19.6 | 66.9 |
| 4-5 Pd—Ru/PVP (1:1) | 13.4 | 0.5 | 0.5 | 68.4 | 25.1 | 93.5 |
| 4-6 Pd—Ru/PVP (1:9) | 13.4 | 0.025 | 0.225 | 15.8 | 25.5 | 41.3 |
| 4-7 Pd—Ru/PVP (9:1) | 13.4 | 0.225 | 0.025 | 23.7 | 26.4 | 50.1 |

In Table 4, the amounts of Pd and Ru (mol %) are those determined with respect to bromobenzene. The amounts of PVP (mass %) are those calculated by the formula PVP/(PVP+Metals). These are the same for Table 5 shown below.

When comparing 4-1 (Pd fine particles), 4-2 (Ru fine particles), and 4-4 ($Pd_{0.5}$—$Ru_{0.5}$ alloy fine particles) for which the total amount of the catalyst is equal, it is seen that the yield of the cross-coupling was highest in the case of using the $Pd_{0.5}$—$Ru_{0.5}$ alloy fine particles. In addition, when comparing 4-4 ($Pd_{0.5}$—$Ru_{0.5}$ alloy fine particles), 4-6 ($Pd_{0.1}$—$Ru_{0.9}$ alloy fine particles), and 4-7 ($Pd_{0.9}$—$Ru_{0.1}$ alloy fine particles) for which the total amount of the catalyst is equal and the composition of the Pd—Ru alloy fine particles is different, it is seen that the yield of the cross-coupling was highest in the case of using the $Pd_{0.5}$—$Ru_{0.5}$ alloy fine particles.

Example 7

In Example 7, the catalytic activity of Pd—Ru alloy fine particles for Suzuki-Miyaura cross-coupling was evaluated for different alloy compositions using a different solvent. In Example 7, the reaction was performed under the conditions shown below. The procedures for the reaction were the same as those in Example 4. As the catalysts, $Pd_{0.5}$—$Ru_{0.5}$ alloy fine particles, $Pd_{0.1}$—$Ru_{0.9}$ alloy fine particles, and $Pd_{0.9}$—$Ru_{0.1}$ alloy fine particles were used. These were fine particles fabricated by the method described above and were protected by PVP.

Starting materials and their amounts: Same as those in Example 4

Amounts of catalyst and PVP: As listed in Table 5

Solvent: Mixed solvent of N,N-dimethylacetamide (3 mL) and water (3 mL)

Base: $K_2CO_3$ (3 mmol)

Reaction temperature: 100° C.

Reaction time: 5 minutes

As comparative examples, similar evaluations were made using Pd fine particles and Ru fine particles instead of the alloy fine particles. Some of the reaction conditions and the evaluation results are shown in Table 5.

TABLE 5

| Catalyst No. (Pd:Ru ratio) | PVP (%) | Pd (mol %) | Ru (mol %) | Yield | | |
|---|---|---|---|---|---|---|
| | | | | (3) Cross-coupling (%) | (4) Homocoupling (%) | Total (%) |
| 5-1 Pd/PVP (1:0) | 13.7 | 0.25 | 0 | 91.5 | 9.0 | 100.5 |
| 5-2 Pd/PVP (1:0) | 13.7 | 0.5 | 0 | 100.0 | 20.6 | 120.6 |
| 5-3 Ru/PVP (0:1) | 13.8 | 0 | 0.5 | 0.0 | 29.6 | 29.6 |
| 5-4 Pd—Ru/PVP (1:1) | 13.4 | 0.25 | 0.25 | 100.0 | 8.2 | 108.2 |
| 5-5 Pd—Ru/PVP (1:1) | 13.4 | 0.125 | 0.125 | 100.0 | 8.2 | 108.2 |
| 5-6 Pd—Ru/PVP (1:1) | 13.4 | 0.08 | 0.08 | 100.0 | 8.7 | 108.7 |
| 5-7 Pd—Ru/PVP (1:1) | 13.4 | 0.04 | 0.04 | 97.0 | 9.1 | 106.1 |
| 5-8 Pd—Ru/PVP (1:1) | 13.4 | 0.25 | 0.25 | 100.0 | 8.5 | 108.5 |
| 5-9 Pd—Ru/PVP (9:1) | 13.5 | 0.225 | 0.025 | 100.0 | 6.4 | 106.4 |
| 5-10 Pd—Ru/PVP (1:9) | 13.5 | 0.025 | 0.225 | 100.0 | Trace amount | 100.0 |
| 5-11 Pd—Ru/PVP (1:9) | 13.5 | 0.0083 | 0.075 | 82.6 | 11.9 | 94.5 |

When comparing 5-2 (Pd fine particles), 5-3 (Ru fine particles), and 5-4 ($Pd_{0.5}$—$Ru_{0.5}$ alloy fine particles) for which the total amount of the catalyst is equal, it is seen that the yield of the cross-coupling was maximum in the case of using the Pd fine particles and in the case of using the $Pd_{0.5}$—$Ru_{0.5}$ alloy fine particles. In addition, as shown by the results for 5-1 (Pd fine particles), 5-5 ($Pd_{0.5}$—$Ru_{0.5}$ alloy fine particles), 5-9 ($Pd_{0.1}$—$Ru_{0.9}$ alloy fine particles), and 5-10 ($Pd_{0.9}$—$Ru_{0.1}$ alloy fine particles) for which the total amount of the catalyst is equal and the composition of the Pd—Ru alloy fine particles is different, the yield of the cross-coupling was maximum in the case of using the $Pd_{0.5}$—$Ru_{0.5}$ alloy fine particles, in the case of using the $Pd_{0.1}$—$Ru_{0.9}$ alloy fine particles, and in the case of using the $Pd_{0.9}$—$Ru_{0.1}$ alloy fine particles. The yield of the homocoupling was minimum in the case of using the $Pd_{0.9}$—$Ru_{0.1}$ alloy fine particles.

Example 8

In Example 8, the catalytic activity of Pd—Ru alloy fine particles for Suzuki-Miyaura cross-coupling was evaluated using different starting materials. In Example 8, the reaction was performed under the conditions shown below. The $Pd_{0.5}$—$Ru_{0.5}$ alloy fine particles used were those protected by PVP as in Example 4.

Starting materials and their amounts: As described below
Catalyst and its amount: $Pd_{0.5}$—$Ru_{0.5}$ alloy fine particles (0.2 mg (Pd: 0.08 mol %, Ru: 0.08 mol %)
Solvent: Mixed solvent of N,N-dimethylacetamide (3 mL) and water (3 mL)
Base: $K_2CO_3$ (3 mmol)
Reaction temperature: 100° C.
Reaction time: As listed in Table 6

As the starting materials, 1.0 mmol of the compound (A) represented by the above formula (I) and 1.2 mmol of the compound (B) represented by the above formula (II) were used. The substituents $R^2$, X, and $R^4$ are as shown in Table 6. Some of the reaction conditions and the evaluation results are shown in Table 6.

TABLE 6

| | Compound of formula (I) | | Compound of formula (II) | Reaction time | Reaction product | | Total yield |
|---|---|---|---|---|---|---|---|
| | | | | | Product and yield (%) of cross-coupling | Product and yield (%) of homo-coupling | |
| No. | $R^2$ | X | $R^4$ | (minute) | | | (%) |
| 6-1 | H | Br | Me | 5 | 3a, 98.2 | 4a, 8.8 | 107 |
| 6-2 | H | I | Me | 5 | 3a, 100 | 0.0 | 100 |
| 6-3 | H | Cl | Me | 240 | 3a, 10.7 | 4a, 17.3 4b, 4.3 | 31.9 |
| 6-4 | Me | Br | H | 5 | 3a, 100 | 4b, 0 | |
| 6-5 | Me | Br | Me | 5 | 3b, (*1) | 4a, 109 | |
| 6-6 | Me | Br | OMe | 5 | 3c, 77.5 | 4c, 0.0 | 77.5 |
| 6-7 | OMe | Br | H | 5 | 3d, 99 | 4c, trace amount | >99 |
| 6-8 | OMe | Br | Me | 5 | 3c, 97.4 | 4a, 0.0 | 97.4 |
| 6-9 | OMe | Br | OMe | 5 | (*1) | 4c, 64.7 (*1) | 64.7 |
| 6-10 | COMe | Br | H | 5 | 3e, 100 | 4b, 0.0 | 100 |
| 6-11 | COMe | Br | Me | 5 | 3f, 100 | 4a, 0.0 | 100 |
| 6-12 | COMe | Br | OMe | 5 | 3g, 100 | 4c, 0.0 | 100 |
| 6-13 | H | I | OMe | 5 | 3d, 100 | 4c, 2.3 | 102.3 |
| 6-14 | H | I | H | 5 | (*1) | 4b, 100 (*1) | 100 |
| 6-15 | H | Br | H | 5 | (*1) | 4b, 100 (*1) | 100 |
| 6-16 | H | Br | OMe | 5 | 3d, 70.4 | 4c, 8.9 | 79.3 |

In this table, Me denotes a methyl group, OMe denotes a methoxy group, and COMe denotes an acetyl group.
(*1) The cross-coupling product and the homocoupling product are the same. The yield shown in the cell for homocoupling includes the yield of the cross-coupling.

The structures of the reaction products denoted by reference characters in Table 6 are shown below.

[Chemical formula 4]

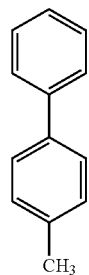

3a

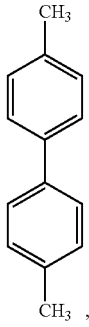

3b

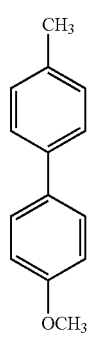

4a

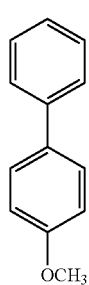

3c

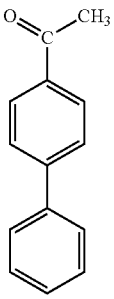

3d

3e

-continued

3f
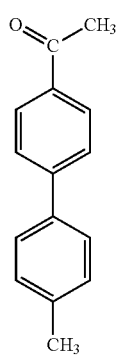

3g
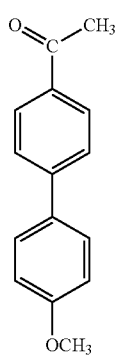

4c
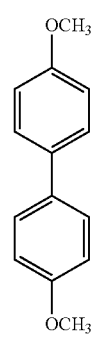

4b
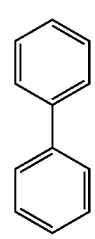

Example 9

In Example 9, the TOF (Turn Over Frequency) of Pd—Ru alloy fine particles ($Pd_{0.5}$—$Ru_{0.5}$) for Suzuki-Miyaura cross-coupling was evaluated. In Example 9, the reaction was performed under the conditions shown in Table 7. The $Pd_{0.5}$—$Ru_{0.5}$ alloy fine particles used were those protected by PVP as in Example 4. The cross-coupling reaction carried out in Example 9 is represented by the following formula.

[Chemical formula 5]

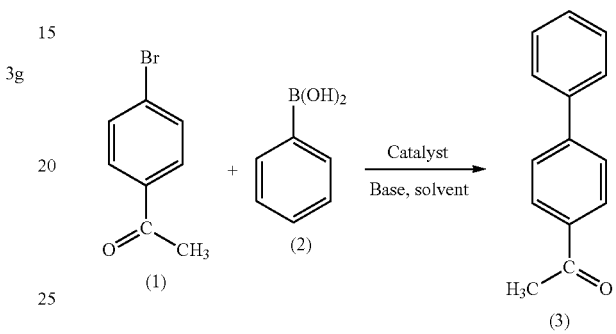

The reaction conditions and the evaluation results are shown in Table 7. In 7-1 and 7-2, the $Pd_{0.5}$—$Ru_{0.5}$ alloy fine particles were added in such an amount that the Pd and Ru contents were each 0.1 mg (0.2 mg in total) with respect to bromobenzene. The p-bromoacetophenone (1 mmol) represented by the formula (1) and the phenylboronic acid (1.2 mmol) represented by the formula (2) were reacted.

TABLE 7

| No. | Catalyst | Base (Amount) | Solvent (Amount) | Reaction temperature (° C.) | Reaction time (minutes) | (3) Amount of cross-coupling product (mmol) | TOF ($h^{-1}$) |
|---|---|---|---|---|---|---|---|
| 7-1 | $Pd_{0.5}$—$Ru_{0.5}$ ($2.5 \times 10^{-3}$) (*1) | $K_2CO_3$ (3 mmol) | EtOH (3.0 mL) + Water (3.0 mL) | Room temperature | 10 | 0.783 | 1879 |
| 7-2 | $Pd_{0.5}$—$Ru_{0.5}$ ($8 \times 10^{-4}$) (*1) | $K_2CO_3$ (3 mmol) | DMA (3.0 mL) + Water | 100 | 5 | 1.0 | 15000 |

TABLE 7-continued

| No. | Catalyst | Base (Amount) | Solvent (Amount) | Reaction temperature (° C.) | Reaction time (minutes) | (3) Amount of cross-coupling product (mmol) | TOF (h$^{-1}$) |
|---|---|---|---|---|---|---|---|
| | | | (3.0 mL) | | | | |

(*1) Molar amount of Pd contained in the catalyst

For comparison, the cross-coupling reaction was performed using other catalysts than the Pd—Ru alloy fine particles. The starting materials were the same as those used in 7-1 and 7-2; however, their amounts were changed. Specifically, the p-bromoacetophenone (1 mmol) represented by the formula (1) and the phenylboronic acid (1.5 mmol) represented by the formula (2) were reacted. The reaction conditions and the evaluation results are shown in Table 8.

TABLE 8

| No. | Catalyst (Amount of catalyst) | Base (Amount) | Solvent (Amount) | Reaction temperature (° C.) | Reaction time | (3) Amount of cross-coupling product (mmol) | TOF (h$^{-1}$) |
|---|---|---|---|---|---|---|---|
| 7-3 | Pd fine particles (2 mmol) | K$_2$CO$_3$ (2 mmol) | C$_3$OH (5 mL) + CH$_3$CN (5 mL) | Room temperature | 2 hours | 0.93 | 0.23 |
| 7-4 | [Pd$^{2+}$OAc$_2$]L$_2$ 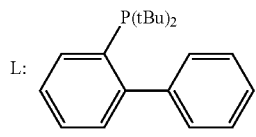 (1 × 10$^{-5}$ mmol) | K$_3$PO$_4$ (2 mmol) | Toluene (9 mL) | 100 | 19 hours | 1.0 | 5263 |

As shown in Table 7, the TOFs of the Pd—Ru alloy fine particles were much higher than those of the catalysts shown in Table 8.

Example 10

In Example 10, Pd—Ru alloy fine particles supported on a support were evaluated for their catalytic activity for Suzuki-Miyaura cross-coupling reaction.

A catalyst including Pd—Ru alloy fine particles supported on a support was fabricated in the same manner as in Example 1. By the use of this catalyst, the two compounds (bromobenzene and phenylboronic acid) used in 6-15 in Table 6 were reacted. The reaction conditions and the evaluation results are shown in Table 9. In Table 9, the results for 6-15 in Table 6 are also shown for comparison.

Although, in Table 9, only the amount of Pd is shown as the amount of the catalyst, the amount of Ru is the same as the amount of Pd.

TABLE 9

| | Starting materials | | Solvent | Reaction | | Amount of | |
|---|---|---|---|---|---|---|---|
| No. | Bromobenzene (mmol) | Phenylboronic acid (mmol) | DMA/H$_2$O (mL/mL) | temperature Reaction time | Amount of Pd (mmol) | product (mmol) | TOF (h$^{-1}$) |
| 9-1 | 15.625 | 18 | 45/45 | 100° C. 60 minutes | 1.16 × 10$^{-4}$ (with support) | 10.02 | 86,379 |
| 6-15 | 1 | 1.2 | 3/3 | 100° C. 5 minutes | 8.0 × 10$^{-4}$ (without support) | 1.00 | 15,000 |

As shown in Table 9, the Pd—Ru alloy fine particles exhibited excellent catalytic activity also when they were supported on a support.

Example 11

Catalytic Activity as Three-Way Catalyst

Noble metal-supported catalysts using Pd—Ru alloy fine particles were fabricated in the same manner as described above. The compositions of the Pd—Ru alloy fine particles were those represented by $Pd_{0.1}$—$Ru_{0.9}$, $Pd_{0.3}$—$Ru_{0.7}$, $Pd_{0.5}$—$Ru_{0.5}$, $Pd_{0.7}$—$Ru_{0.3}$, and $Pd_{0.9}$—$Ru_{0.1}$. For each of the fabricated catalysts, its catalytic activity for reduction reaction of nitrogen oxide ($NO_X$), its catalytic activity for oxidation reaction of carbon monoxide (CO), and its catalytic activity for oxidation reaction of hydrocarbon ($C_3H_6$) were simultaneously evaluated. For comparison, other noble metal-supported catalysts were fabricated in the same manner as described above, except that other fine particles were used instead of the Pd—Ru alloy fine particles. As the fine particles substituting for the Pd—Ru alloy fine particles, Ru fine particles, Pd fine particles, and a physical mixture of Ru fine particles and Pd fine particles were used.

The evaluation of the catalytic activity as a three-way catalyst was performed using a fixed-bed flow reactor. Specifically, first, 200 mg of the catalyst formed into pellets was loaded in a quartz reaction tube with an inner diameter of 7 mm by means of quartz wool. This reaction tube was connected to the reactor, and then a $N_2$-based mixed gas with a theoretical air-fuel ratio (NO:993 ppm, $O_2$:0.6%, CO:0.6%, $C_3H_6$:555 ppm, $CO_2$:14.1%, $H_2$:0.2%, $N_2$:balance gas), which was a simulant of exhaust gas of automobiles, was fed at a flow rate adjusted so that the space velocity was 60 liters/(h·$g_{cat}$) (the total flow rate was 200 ml/min). The catalyst layer had room temperature at the start of the feed of the mixed gas. From the start of the feed of the mixed gas, the temperature of the catalyst layer was increased from room temperature to 600° C. at a rate of 10° C./minute, while the concentrations of $NO_X$, CO, and $C_3H_6$ contained in the collected gas were successively measured using a multi-gas analyzer (VA-3000 manufactured by HORIBA, Ltd.) at intervals of 30 seconds.

Figure 15A:
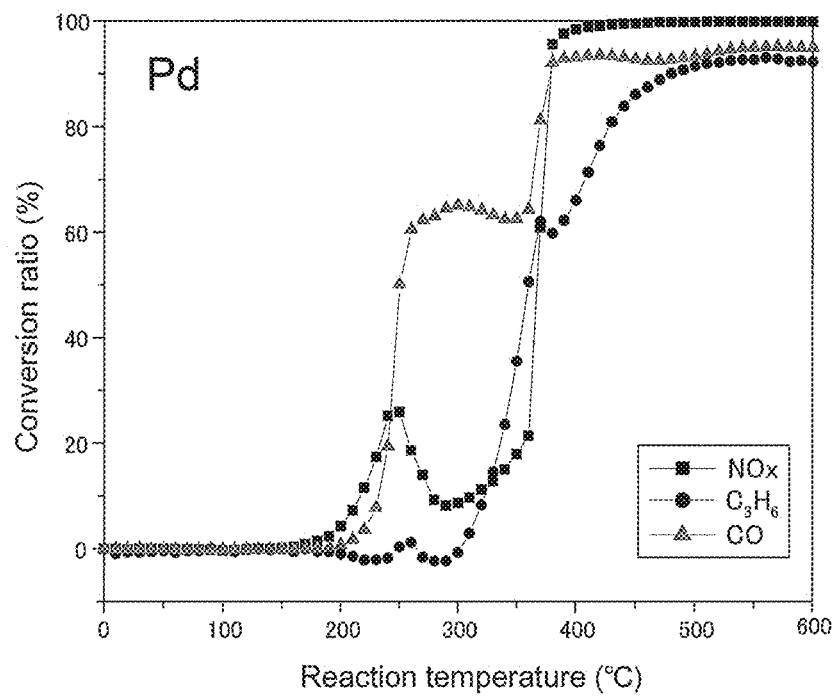
FIG. 15A is a graph showing the catalytic activity of a noble metal-supported catalyst using Pd fine particles.
Figure 15B:
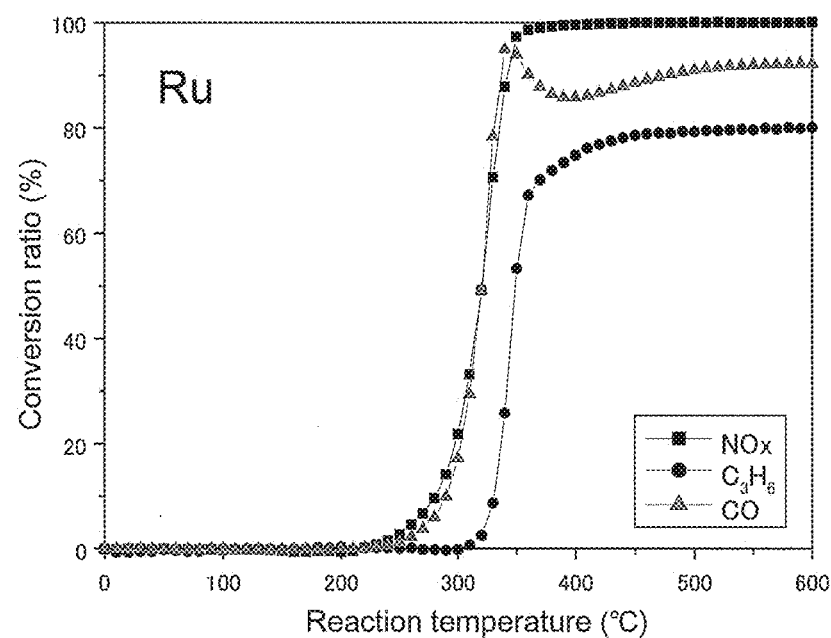
FIG. 15B is a graph showing the catalytic activity of a noble metal-supported catalyst using Ru fine particles.
Figure 15C:
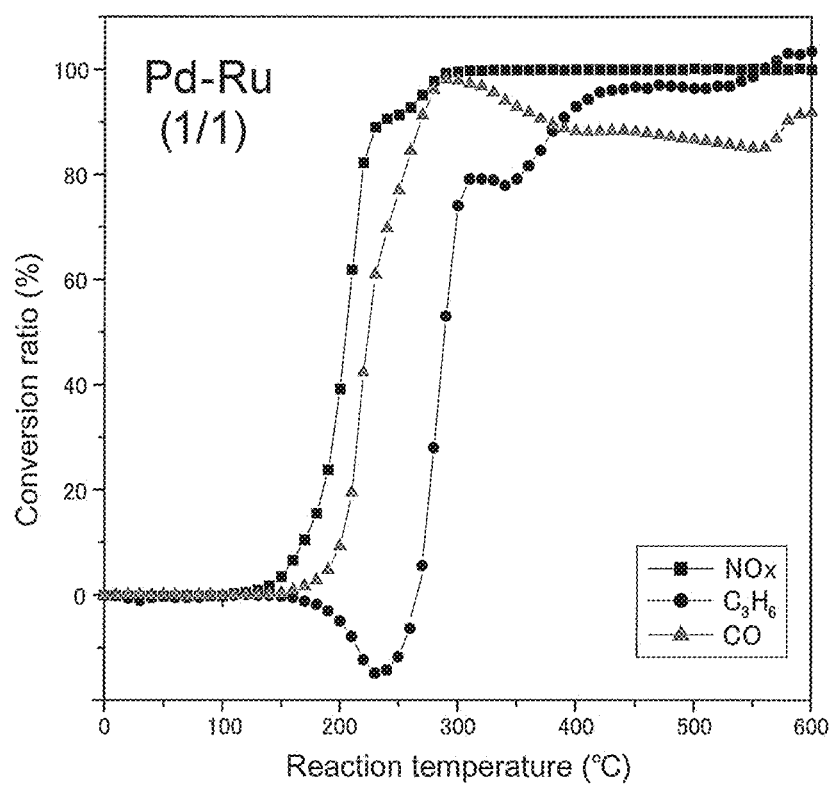
FIG. 15C is a graph showing the catalytic activity of a noble metal-supported catalyst using Pd—Ru alloy fine particles ($Pd_{0.5}$—$Ru_{0.5}$).

The measurement results are shown in FIG. 15A to FIG. 15C. FIG. 15A is a graph showing the catalytic activity of the noble metal-supported catalyst using the Pd fine particles. FIG. 15B is a graph showing the catalytic activity of the noble metal-supported catalyst using the Ru fine particles. FIG. 15C is a graph showing the catalytic activity of the noble metal-supported catalyst using the Pd—Ru alloy fine particles ($Pd_{0.5}$—$Ru_{0.5}$). Specifically, the vertical axes of FIG. 15A to FIG. 15C represent the proportion of nitrogen oxide having been converted, the proportion of carbon monoxide having been converted, and the proportion of hydrocarbon having been converted. In this experiment, components (particularly propylene) adsorbed on the catalyst at low temperatures is desorbed with increase in temperature. This may cause the conversion ratio of HC to be below 0%.

As shown in FIG. 15A, when the Pd fine particles were used, the conversion of $NO_X$ was initiated at a relatively low temperature; however, the conversion ratio of $NO_X$ dropped temporarily in the temperature range of 250° C. to 350° C. This is because CO becomes preferentially reactive with $O_2$. In addition, around 400° C., the oxidation reaction of CO plateaued due to deactivation of Pd. As shown in FIG. 15B, when the Ru fine particles were used, the temperatures at which the reaction of $NO_X$ and the reaction of CO initiated were increased, compared with the reaction initiation temperature in the case of using the Pd fine particles. In addition, the conversion ratio of $C_3H_6$ did not reach 100%. This shows that the HC oxidation activity of the Ru fine particles is low. As shown in FIG. 15C, when the Pd—Ru alloy fine particles were used, the reaction of $NO_X$ and the reaction of CO were initiated at lower temperatures than those at which the reactions were initiated in the case of using the Pd fine particles and in the case of using the Ru fine particles. In addition, the Pd—Ru alloy fine particles had also excellent $C_3H_6$ decomposition property.

Figure 16A:
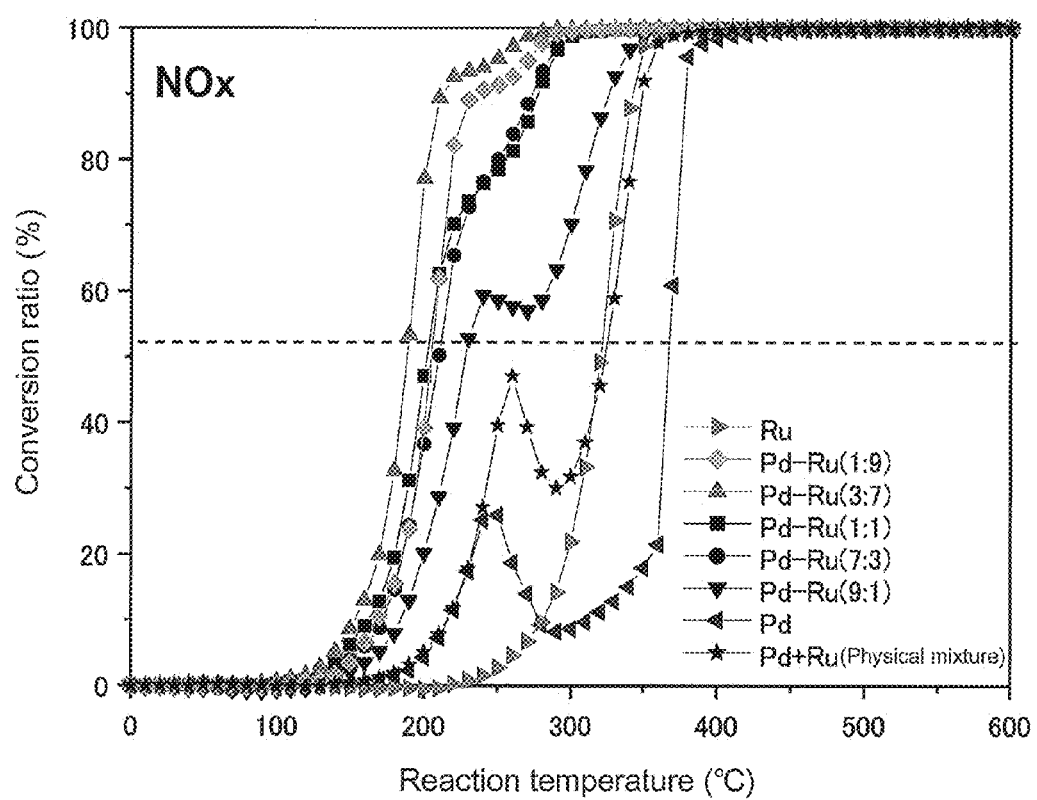
FIG. 16A is a graph showing the catalytic activity for reduction reaction of nitrogen oxide for various fine particles.
Figure 16B:
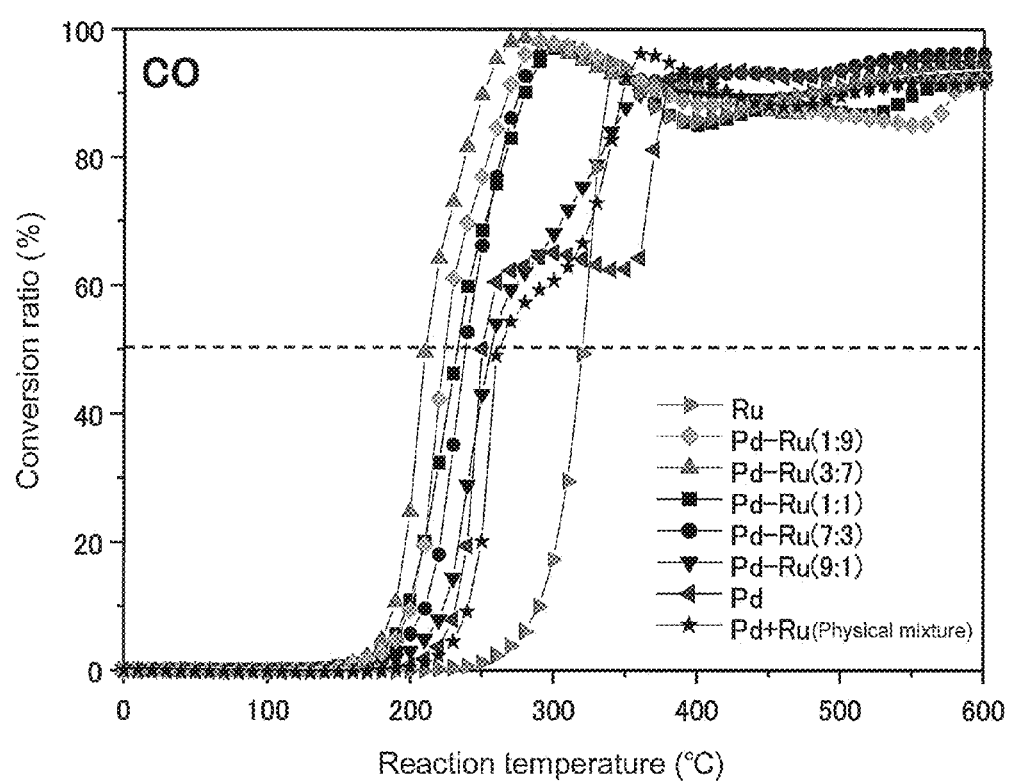
FIG. 16B is a graph showing the catalytic activity for oxidation reaction of carbon monoxide for various fine particles.
Figure 16C:
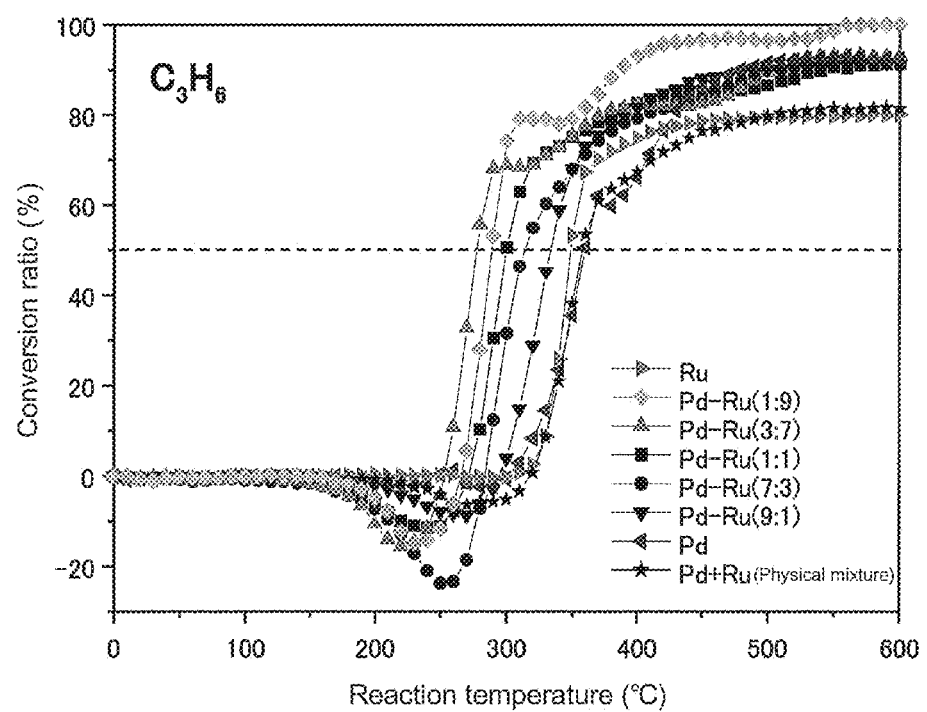
FIG. 16C is a graph showing the catalytic activity for oxidation reaction of hydrocarbon for various fine particles.

FIG. 16A is a graph showing the catalytic activity for reduction reaction of nitrogen oxide ($NO_X$) for the various fine particles. FIG. 16B is a graph showing the catalytic activity for oxidation reaction of carbon monoxide (CO) for the various fine particles. FIG. 16C is a graph showing the catalytic activity for oxidation reaction of hydrocarbon ($C_3H_6$) for the various fine particles. The vertical axis of FIG. 16A represents the proportion of nitrogen oxide having been converted. The vertical axis of FIG. 16B represents the proportion of carbon monoxide having been converted. The vertical axis of FIG. 16C represents the proportion of hydrocarbon having been converted.

As shown in FIG. 16A, when the Pd content was large, a decrease in activity around 250° C. was prominently observed. Furthermore, addition of 10 mol % of Pd to Ru significantly increased the activity. From FIG. 16B, it can be understood that the decrease in CO oxidation capacity, as observed when the Pd content was large, was reduced by the coexistence of Ru. Furthermore, addition of 10 mol % of Pd to Ru significantly increased the activity. As shown in FIG. 16C, the Pd—Ru alloy fine particles exhibited high decomposition activity for hydrocarbon as in the case of $NO_X$ or CO.

Figure 17A:
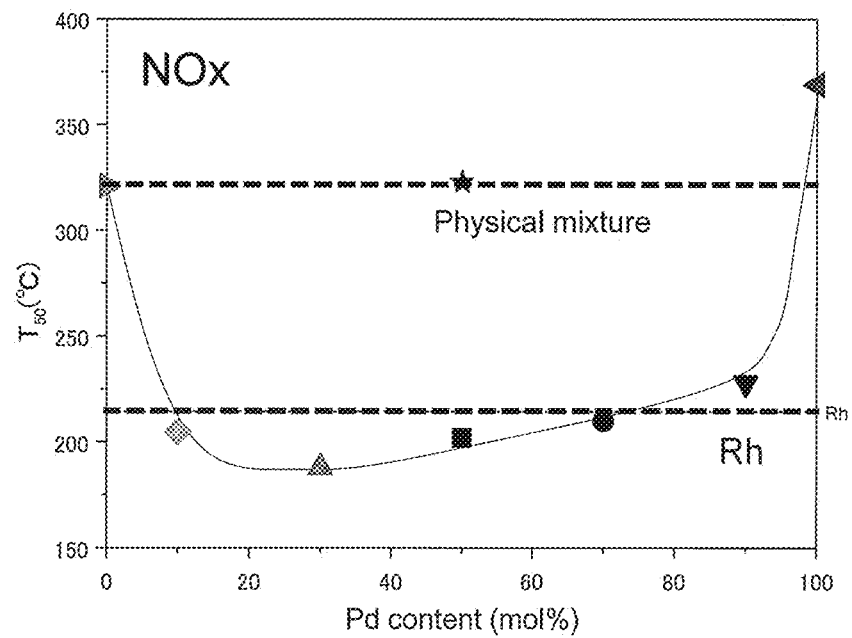
FIG. 17A is a graph showing the $T_{50}$ in reduction reaction of nitrogen oxide for various fine particles.
Figure 17B:
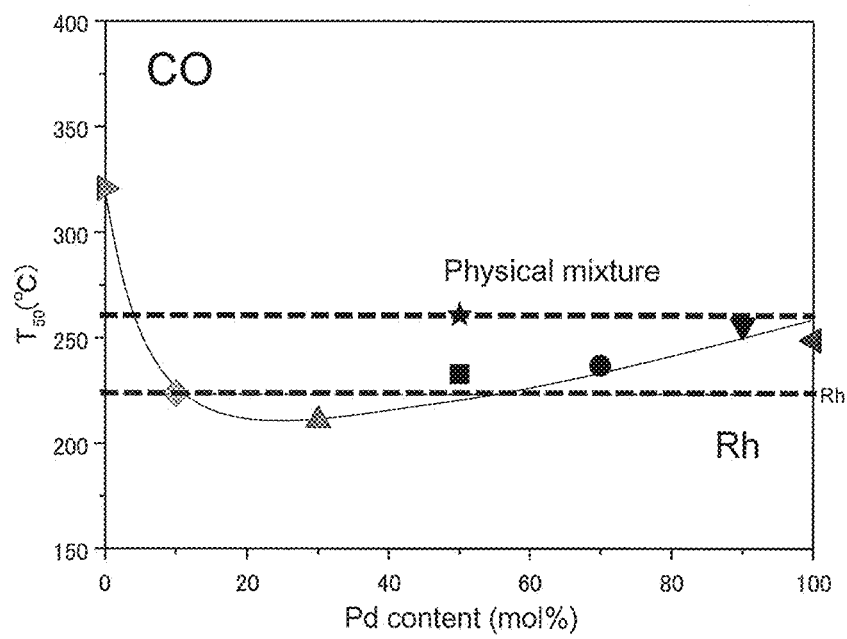
FIG. 17B is a graph showing the $T_{50}$ in oxidation reaction of carbon monoxide for various fine particles.
Figure 17C:
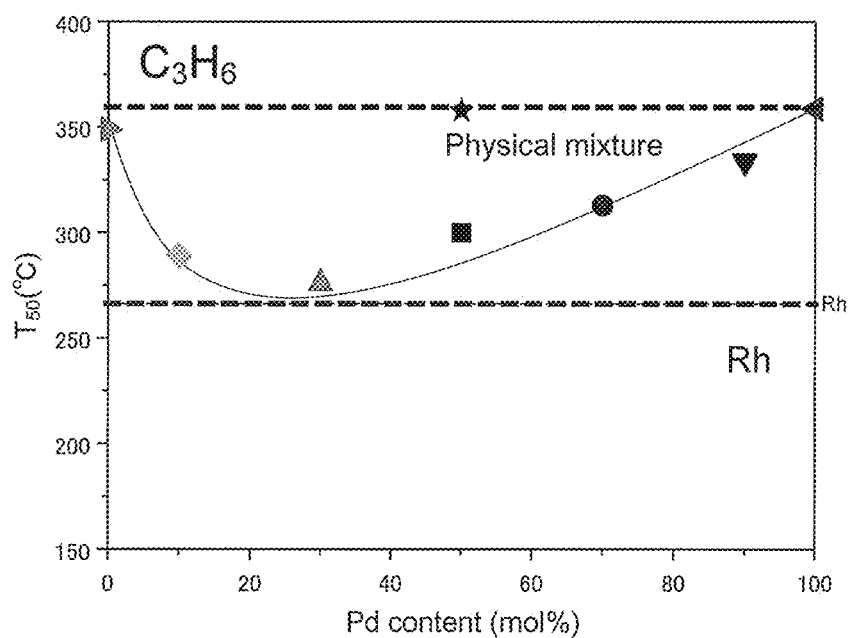
FIG. 17C is a graph showing the $T_{50}$ in oxidation reaction of hydrocarbon for various fine particles.

FIG. 17A is a graph showing the $T_{50}$ (° C.) in reduction reaction of nitrogen oxide ($NO_X$) for the various fine particles. FIG. 17B is a graph showing the $T_{50}$ (° C.) in oxidation reaction of carbon monoxide (CO) for the various fine particles. FIG. 17C is a graph showing the $T_{50}$ (° C.) in oxidation reaction of hydrocarbon ($C_3H_6$) for the various fine particles. The vertical axis "$T_{50}$ (° C.)" of each graph represents temperatures at which the conversion ratio of 50% can be achieved. For reference, a catalyst using Rh fine particles was fabricated in the same manner as described above, and was examined for $T_{50}$. In each graph, the $T_{50}$ for Rh fine particles and the $T_{50}$ for a physical mixture of Ru fine particles and Pd fine particles are shown by dashed lines.

As shown in FIG. 17A to FIG. 17C, the Pd—Ru alloy fine particles exhibited high purification activity for the three components, $NO_X$, CO, and HC. In particular, the $NO_X$ purification capacity and CO purification capacity of the Pd—Ru alloy fine particles surpassed the $NO_X$ purification capacity and CO purification capacity of the Rh fine particles in some cases. With a particular composition ($Pd_{0.3}$—$Ru_{0.7}$), the Pd—Ru alloy fine particles had a HC purification capacity comparable to the HC purification capacity of Rh fine particles. In addition, for every composition, the Pd—Ru alloy fine particles exhibited higher activity than the physical mixture of Pd and Ru. It is thought that, in order to increase the catalytic activity, it is important, as in the present invention, to form a solid solution of Pd and Ru so that Pd and Ru are positioned close to each other. As is understood from FIG. 17A to FIG. 17C, the molar ratio of Pd contained in the Pd—Ru alloy is preferably 0.1 or more but less than 0.7, and more preferably 0.1 or more but less than 0.5.

As described above, the Pd—Ru alloy fine particles of the present invention exhibit high purification activity for the three components, $NO_X$, CO, and HC. The Pd—Ru alloy fine particles exhibit high activity as an oxidation catalyst and as a reduction catalyst. Therefore, a catalyst obtained by allowing the Pd—Ru alloy fine particles as a noble metal material to be supported on a support can be used as a three-way catalyst instead of conventional three-way catalysts (e.g., catalysts using Pd, Pt, or Rh). Depending on circumstances, only the Pd—Ru alloy fine particles may be supported on a support as a noble metal material. The support is a ceramic support, and is in the form of, for example, a honeycomb or particles. The three-way catalyst may contain a co-catalyst such as a rare earth oxide together with the Pd—Ru alloy fine particles.

INDUSTRIAL APPLICABILITY

The present invention can be used for a catalyst including Pd—Ru solid solution alloy fine particles and a method for producing Pd—Ru solid solution alloy fine particles. The present invention can be used also for a method for producing an organic compound by using the catalyst.

The present invention can provide a method using Pd—Ru solid solution alloy fine particles as at least one selected from the group consisting of an oxidation catalyst for carbon monoxide, a reduction catalyst for nitrogen oxide, an oxidation catalyst for hydrogen gas, an oxidation catalyst for hydrocarbon, and a catalyst for Suzuki-Miyaura cross-coupling.

The invention claimed is:

1. A catalyst comprising palladium-ruthenium solid solution alloy fine particles in which palladium and ruthenium form a solid solution at an atomic level.

2. The catalyst according to claim 1, wherein the alloy fine particles have a composition represented by $Pd_x$—$Ru_{1-x}$, where x satisfies $0.1 \leq x \leq 0.9$.

3. A method of catalyzing carbon monoxide oxidation, comprising contacting carbon monoxide with the catalyst according to claim 1.

4. A method of catalyzing nitrogen oxide reduction, comprising contacting nitrogen oxide with the catalyst according to claim 1.

5. A method of catalyzing oxidation of hydrogen gas, comprising contacting hydrogen gas with the catalyst according to claim 1.

6. A method of catalyzing oxidation of hydrocarbon, comprising contacting hydrocarbon with the catalyst according to claim 1.

7. A method of catalyzing Suzuki-Miyaura cross-coupling reaction, comprising contacting a compound A of formula $R^1$—X and a compound B of formula $R^3$-G with the catalyst according to claim 1, wherein $R^1$ and $R^3$ are each independently an aryl group;
X is halogen; and
G is —$B(OH)_2$ or esters thereof, or —$BR^aR^b$, wherein $R^a$ and $R^b$ are each independently an alkyl group.

8. The catalyst according to claim 1, wherein the solid solution alloy fine particles each have a fcc structure and a hcp structure, and the fcc structure and the hcp structure in each of the palladium-ruthenium solid solution alloy fine particles have substantially equal composition ratios.

9. The catalyst according to claim 8, wherein the solid solution alloy fine particles have a composition represented by $Pd_x$—$Ru_{1-x}$, where x satisfies $0.3 \leq x \leq 0.7$.

10. The method accordingly to claim 7, wherein $R^1$ is a phenyl group or a phenyl group to which a substituent is bonded.

11. The method according to claim 10, wherein the substituent is a trimethylsilyl group, a triflate group, or a tosyl group.

12. The method accordingly to claim 7, wherein $R^3$ is a phenyl group or a phenyl group to which a substituent is bonded.

13. The method accordingly to claim 7, wherein the compound A has a structure of formula (I), and the compound B has a structure of formula (II)

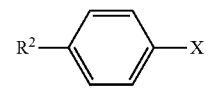

(I)

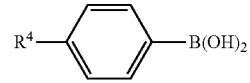

(II)

wherein
$R^2$ is selected from the group consisting of hydrogen, methyl, methoxy, acetyl, cyano, fluoro, and nitro;
X is selected from the group consisting of I, Br, and Cl; and
$R^4$ is selected from the group consisting of hydrogen, methyl, methoxy, cyano, fluoro, and nitro.

14. The method accordingly to claim 7, wherein the compound A and the compound B are cross-coupled in a solvent in the presence of the catalyst according to claim 1 and a base.

* * * * *